United States Patent [19]
Berka et al.

[11] Patent Number: 5,874,275
[45] Date of Patent: Feb. 23, 1999

[54] POLYPEPTIDES HAVING MUTANASE ACTIVITY AND NUCLEIC ACIDS ENCODING SAME

[75] Inventors: Randy M Berka, Davis, Calif.; Stephan Christgau, Gentofte; Torben Halkier, Frederiksberg C, both of Denmark; Jeff Shuster, Davis, Calif.; Claus Crone Fuglsang, Copenhagen, Denmark

[73] Assignees: Novo Nordisk A/S, Bagsvaerd, Denmark; Novo Nordisk Biotech, Inc., Davis, Calif.

[21] Appl. No.: 956,268

[22] Filed: Oct. 22, 1997

Related U.S. Application Data

[62] Division of Ser. No. 797,366, Feb. 7, 1997, Continuation-in-part of Ser. No. 598,881, Feb. 9, 1996, abandoned.

[51] Int. Cl.$^6$ .............................. C12N 9/24; C12N 1/20; C12N 15/00; C07H 21/04
[52] U.S. Cl. ................ 435/200; 435/252.33; 435/320.1; 435/933; 435/935; 536/23.2; 536/23.7; 530/350; 424/50; 424/94.6
[58] Field of Search ................ 435/200, 252.33, 435/320.1, 933, 935; 536/23.2, 23.7; 530/350; 424/50, 94.6

[56] References Cited

U.S. PATENT DOCUMENTS 4,353,891  10/1982  Guggenheim et al. ................ 424/50

OTHER PUBLICATIONS

Edman et al. Eur. J. Biochem. 1 : 80–91, 1967.
Suggs et al. PNAS, USA. 78 (11) : 6613–17, 1981.

*Primary Examiner*—Robert A. Wax
*Assistant Examiner*—Tekchand Saidha
*Attorney, Agent, or Firm*—Steve T. Zelson, Esq.; Valeta Gregg, Esq.

[57] ABSTRACT

The present invention relates to polypeptides having mutanase activity and isolated nucleic acid sequences encoding the polypeptides. The invention also relates to nucleic acid constructs, vectors, and host cells comprising the nucleic acid sequences as well as methods for producing the polypeptides. The present invention further relates to oral cavity compositions and methods for degrading mutan.

22 Claims, 10 Drawing Sheets

FIG. 3A

```
AATTGTGCCCTAAACCTCCTCCTGGAGGAACACACTCAAGATGAAAGTCTCCAGTGCCTTCGGCGGACGCTGTCCGCAATTATAGCTGCGTGCTCAGCT  100
                          M  K  V  S  S  A  F  A  A  T  L  S  A  I  I  A  A  C  S  A

CTTCCTTCTGACTCAATGGTTTCGAGGCGAAGCACATCGGACCGTCTCGTGTTCGCCATTTCATGGTAAACATCATCTCGAATATGAGGCACATAGTC  200
 L  P  S  D  S  M  V  S  R  R  S  T  S  D  R  L  V  F  A  H  F  M

AGTGACGATAGATTG CTGAC TTCATCAGGTTGGTATCGTCAGTGACCGGACCAGTGCTAGCGATTATGACGCCGACATGCAGGGTGCTAAAGCTTATGG  300
                              V  G  I  V  S  D  R  T  S  A  S  D  Y  D  A  D  M  Q  G  A  K  A  Y  G

AATTGACGCCCTTTGCATTGAATATCGGTACCGATACCTTCAGCGACCAGCAACTGGGGTATGCCTACGAGTCTGCGGCAAACAATGACATGAAAGTGTTC  400
 I  D  A  F  A  L  N  I  G  T  D  T  F  S  D  Q  Q  L  G  Y  A  Y  E  S  A  A  N  N  D  M  K  V  F

ATTTCATTCGATTCAACTGGTGGTCCACCAGCCAGGCCGAAATTGCCAGTCAGTCAGCTGCTGGCGCAATGTGTTCTTCGCTCCAAACTTCCATCC  500
 I  S  F  D  F  N  W  S  T  S  Q  A  T  E  I  G  Q  K  I  A  Q  Y  G  S  L  P  G  Q  L  M  Y  D

ACAAGATTTCGTCTCGTCGTTTGCTGGCGACGGTGTAGACGGTGTGGCAGCGGTAGCGGTGGCCAATGGCAGCGTGGCAGCGGTTCCAACGTT  600
 D  K  I  F  V  S  S  F  A  G  D  G  V  D  V  A  A  L  K  S  A  A  G  G  N  V  F  F  A  P  N  F  H  P

ATCGTATGGTACAGAACCTGTCGGATGTCGATGTCTTCTCAACTGATGGCTGGCTGCAACTGGTAATAACAAGGCTCCAACTGCCGTGCCAACGTT  700
 S  Y  G  T  D  L  S  D  V  D  G  L  L  N  W  M  G  W  P  S  N  G  N  N  K  A  P  T  A  G  A  N  V

ACCGGTGAGGAAGGGGACGAGGAATATAACTGCTTTGGATGGCAAGCCCTACATTGCTCGTCAGTGCGCCTAACCTACCTCCTAGCCTTGGAGCAAAA  800
 T  V  E  E  G  D  E  E  Y  I  T  A  L  D  G  K  P  Y  I  A

CGATTCAGTTG CTGAC CTTTCTTTTCTTTCTTACTAGCGCCTACGCATTTGGGCCAGAGGTGACATACAGCAAGAACTG  900
                        P  A  S  P  W  F  S  T  H  F  G  P  E  V  T  Y  S  K  N  W
```

FIG. 3B

```
GGTTTCCCATCTGATTTGCTTTCTACCAGCGTTGAATGATCTATTGAATTGGGCCCTCAATTCATTGAAGTGGTCACCTGAATGACTATGGTGAA  1000
 V   F  P  S  D  L  L  F  Y  Q  R  W  N  D  L  L  N  L  G  P  Q  F  I  E  V  V  T  W  N  D  Y  G  E

TCGCAATATGTCGGACCTCTGAACTCTCCTCATACAGACGATGGCTCCTCTCGATGGGCGAATGACATGTAAGCCATCTTGTGTAGGTATCGGTGTTTTG  1100
 S   Q  Y  V  G  P  P  L  N  S  P  H  T  D  D  G  S  S  R  W  A  N  D  M

TTTCTAT CTAAC TCAAGAAACTAGGCCTCTGGCTGATCTGGCAAAGCCCTACATCGCGGCATTCCACGACGGGCCACTTCGCTATCAT  1200
        P   H  D  G  W  L  D  L  A  K  P  Y  I  A  A  F  H  D  G  A  T  S  L  S

CATCCTACAATCACCGAAGACCAGCTCATCTGGTATCGGCCTCAACCACGACTCATGGACTGCGACGCAACTGATACCTGCATGGTTGCTGCCAACAA  1300
 S   S  Y  I  T  E  D  Q  L  I  Y  W  R  P  Q  P  R  L  M  D  C  D  A  T  D  T  C  M  V  A  A  N  N

TGACACGGGCAACTATTCGAGGGCAGACCCAATGGGTGGAAAGCATGGAGGACGCTGTCTTCGTGGTTGCTTTGCTCCAGTCTGCTGGAACGGTTCAG  1400
 S   S  Y  I  T  E  D  Q  L  I  Y  W  R  P  Q  P  R  L  M  D  C  D  A  T  D  T  C  M  V  A  A  N  N

GTCACTTCAGGCCCTAATACCGAGACATTTGATGCTCCTGGTGCAAGCGCCTTCCAGTTCCAAGCGCCTTCGGCGCCCCAGAGCTTCTCCCTGTCGC  1500
 D   T  G  N  Y  F  E  G  R  P  N  G  W  E  S  M  E  D  A  V  F  F  V  V  A  L  L  Q  S  A  G  T  V  Q

GGGATGGCGAGACAGTATTGTCTGGAACAAGCTTTGAAGGATATCATTGATGGATGCTTGTGCGGAATCTACAACTTCAACGCCTATGGTAAGAACTGCCG  1600
 V   T  S  G  P  N  T  E  T  F  D  A  P  A  G  A  S  A  F  Q  V  P  M  G  F  G  P  Q  S  F  S  L  S

GGGATGGCGAGACAGTATTGTCTGGAACAAGCTTTGAAGGATATCATTGATGGATGCTTGTGCGGAATCTACAACTTCAACGCCTATGGTAAGAACTGCCG
 R   D  G  E  T  V  L  S  G  T  S  L  K  D  I  I  D  G  C  L  C  G  I  Y  N  F  N  A  Y

TGTCTTTTGTATATCTGAATATGTTTCCAAGGTT ATTGAC ATGGGAAAAAAAAAAAAAATTCAGTGGGCTCTCTGCCAGCAACTTTCTCCGATCCACTC  1700
                                                                       V  G  S  L  P  A  T  F  S  D  P  L
```

FIG. 3C

```
GAGCCACCTTCTCTCAAGCGCCTTCAGCGAAGGCTTGAAGGTTTCGACATGCAGCGCGACACCATCTTTGGGATTGACATGACCACTCCACCAGAGACCA 1800
 E  P  P  S  L  N  A  F  S  E  G  L  K  V  S  T  C  S  A  T  P  S  L  G  L  T  S  T  T  P  P  E  T

TTCCTACAGGCACGATTACTCCAGGATCAGCTATTACAGGTGCTGCAACAACTACCTCGAACAATCTCGACCACCTCGACGATTCCACGACCTCAACTTT 1900
 F  L  Q  G  T  I  T  P  G  S  A  I  T  G  A  A  T  T  S  T  I  S  T  T  S  T  T  S  T  T  S  T  F

TATCTCAACTACCACCACCACCAGTGCTGTCTACCTCCACCAACCGGAACTTGCATGCGGCACTGGCCCTGACAACTATTCTGGCCTGTGT 2000
 I  P  T  G  T  I  T  P  G  S  A  A  T  T  S  T  I  S  T  T  S  T  T  S  T  T  S  T  F

TATCTCAACTACCACCACCACCAGTGCTGTCTACCTCCACCAACCGGAACTTGCATGCGGCACTGGCCCTGACAACTATTCTGGCCTGTGT 2000
 I  S  T  T  T  T  S  S  A  A  T  S  T  T  G  T  C  I  A  G  T  G  P  D  N  Y  S  G  L  C

TCCTTCTGCTGTAACTACGGCTACTGTCCGGGCTCCGATGGTTCCGATGGCTCCGATGGAGATCCAGTTCCTACGCCTCCAGTAA 2100
 S  F  C  C  N  Y  G  Y  C  P  G  S  D  G  S  A  G  P  C  T  A  Y  G  D  P  V  P  T  P  P  V

CAGGAACAGTTGGCGTTCCGCTTGATGGCGAGGGTGACAGTTACTTGGGTCTGTGTAGTTTGCCTGCAACCACGGCTATTGCCCGTCTACTGCTTGTCA 2200
 Q  E  Q  L  G  V  P  L  D  G  E  G  D  S  Y  L  G  L  C  S  F  A  C  N  H  G  Y  C  P  S  T  A  C  Q

AGTAGAGAGCTGAGAGGTGCCACTATCTAGGTAACATGTTAAAGTAATACCTAGGTACTCTGTGTCTAGCTTGAGAGATGGCAGGTATCTAGTTCT 2300
 V  E  S  .

ATCTTAAATATAAGATTTCTCCAACTTACATGATTTTGATGCACATGGATAGGTAGACCTGGACAGTGAAGGGCAATACTTAAATAATGCAAACAGACAC 2400

TGGATCTATATCGTTCAACTCAGTTGGCCAAAGACTAGTCGTGAAAAAAACACCCTTTGAACAAAAACCTTCTTCGCTGCATCAACGCAGTCCAAAATA 2500

AGTCCAATCCCCTCCACCATGAA 2523
```

FIG. 4A

```
  1  M L G V F R R L R L G A L A A A A L S L G S A A P A N V A I R S L E E R A S S    T. harzianum mut.aa
  1  M - - - - - K V S S A F A A T L S A I - I A A C S A L P S D S M V S R L S T      P. purpurogenum mut.aa 41  A D R L V F C H F M I G I V G D R G S A D Y D D D M Q R A K A A G I D A F A L    T. harzianum mut.aa
 33  S D R L V F A H F M V G I V S D R T S A S D Y D A D M Q G A K A Y G I D A F A L  P. purpurogenum mut.aa 81  N I G V D G Y T D Q Q L G Y A Y D S A D R N G M K V F I S F D F N W W S P G N A  T. harzianum mut.aa
 73  N I G T D T E S D Q O L G Y A Y E S A A N N D M K V F I S F D N W W S T S Q A    P. purpurogenum mut.aa 121  V G V G Q K I A Q Y A N R P A Q L Y V D N R P F A S S F A G D G L D V N A L R S  T. harzianum mut.aa
113  T E I G Q K I A Q Y G S L P G O L M Y D D K I F V S S F A G D G V D V A A L K S  P. purpurogenum mut.aa 161  A A G S N V Y F V P N F H P G Q S S P - S N I D G A L N W M A W D N D G N N K A  T. harzianum mut.aa
153  A A G G N V F F A P N F H P S Y G T D L S D V D G L L N W M G W P S N G N N K A  P. purpurogenum mut.aa 200  P K P G Q T V T V A D G D N A Y K N W L G G K P Y L A P V S P W F F T H F G P E  T. harzianum mut.aa
193  P I A G A N V I V E E G D E E Y I I A L D G K P Y I A P A S P M F S T H F G P E  P. purpurogenum mut.aa 240  V S Y S K N W V F P G G P L T Y N R W Q Q V L Q Q G F P M V E L I V T W N D Y G E  T. harzianum mut.aa
233  V T Y S K N M V F P S D L L F Y Q R W N D L L N L G P O F I E V V I M N D Y G E  P. purpurogenum mut.aa 280  S H Y V G P L K S L H F D D G N S K W V N D M P H D G E L D L S K P F I A A Y K  T. harzianum mut.aa
273  S Q Y V G P L N S P H T D D G S S R W A N D M P H D G W L D L A K P Y I A A F H  P. purpurogenum mut.aa 320  N R D T D I S K - Y V Q N E Q L V Y W Y R R N L K A L D C D A T D T I S N R P A   T. harzianum mut.aa
313  D G A I S L S S S Y I T E D Q L I Y N Y R P Q P R L M D C D A I D I - C M V A A  P. purpurogenum mut.aa
```

FIG. 4B

```
359 N N G S G N Y F E G R P D G W Q T M D D A V Y V A A L L K T I A G S V T I I T S G G   T. harzianum mut.aa
352 N N D T G N Y F E G R P N G W E S M E D A V F V V A L L Q S A G T V Q V I S G P       P. purpurogenum mut.aa 399 I T Q T F L Q A N A G A N L F Q L I P A S I G Q K F A L I R N G Q T I F S G T S L     T. harzianum mut.aa
392 N T E F E D A P A G A S A F Q V P M G F L G P Q S F S L S R D G E I V L S G T S L     P. purpurogenum mut.aa 439 M D I I N V C S C G I Y N F N P Y V G T I P A G F D D P L Q A D G L F S L T I G       T. harzianum mut.aa
432 K D I I D G L C G I Y N F N A Y V G S L P A T E S D P L E P P S L N A F S E G         P. purpurogenum mut.aa 479 L H V I T C L Q A K P S L G T N P P V T S G P V S S L P A S S T T R A S S P P V       T. harzianum mut.aa
472 L K V S I C S A T P S L G L T S I T P P E T I P T G T I T P G S A I T G A A T T       P. purpurogenum mut.aa 519 S S T R V S S P P V S S P P V S R T S S P P P P A S T P P S G Q V C V A G T           T. harzianum mut.aa
512 T S T T S T T S T T S T T F L S T T F L S T T S A A T S I T T G T C T A G T           P. purpurogenum mut.aa 559 V A D G E S G N Y I G L C Q F S C N Y G Y C P - - - - - P G P C K C T A F G A P       T. harzianum mut.aa
552 G P D - - - - N Y S G L C S F C N Y G Y C P G S D G S A G P C T C T A Y G D P         P. purpurogenum mut.aa 594 I S P P A S N G R N G C P L P G E G D G Y L G L C S F S C N H N Y C P P T A C Q       T. harzianum mut.aa
588 V P T P P V T G T V G V P L D G E G D S Y L G L C S F A C N H G Y C P S T A C Q       P. purpurogenum mut.aa 634 Y - - C                                                                               T. harzianum mut.aa
628 V E S .                                                                               P. purpurogenum mut.aa
```

POLYPEPTIDES HAVING MUTANASE ACTIVITY AND NUCLEIC ACIDS ENCODING SAME

CROSS-REFERENCE TO RELATED APPLICATIONS

This application is a divisional of U.S. application Ser. No. 08/797,366 filed Feb. 7, 1997, which is a continuation-in-part of U.S. application Ser. No. 08/598,881 filed Feb. 9, 1996, abandoned, which application is fully incorporated herein by reference.

BACKGROUND OF THE INVENTION

1. Field of the Invention

The present invention relates to polypeptides having mutanase activity and isolated nucleic acid sequences encoding the polypeptides. The invention also relates to nucleic acid constructs, vectors, and host cells comprising the nucleic acid sequences as well as methods for producing the polypeptides. The invention further relates to compositions comprising the polypeptides and methods of use thereof.

2. Description of the Related Art

The formation of dental plaque leads to dental caries, gingival inflammation, periodontal disease, and eventually tooth loss. Dental plaque is a mixture of bacteria, epithelial cells, leukocytes, macrophages, and other oral exudate. The bacteria produce glucans and levans from sucrose found in the oral cavity. These glucans, levans, and microorganisms form an adhesive matrix for the continued proliferation of plaque.

*Streptococcus mutans* is a common bacterium associated with dental plaque. Extracellular insoluble polysaccharides produced by this bacterium in the oral cavity play an important role for adhesion and proliferation of bacteria on the surface of teeth and, hence, may be important in the etiology of dental caries. Mutan is the major component of the insoluble polysaccharides produced by *Streptococcus mutans* and is comprised of a backbone with $\alpha$-1,3-glycosidic linkages and branches with $\alpha$-1,6-glycosidic linkages.

Mutanases are $\alpha$-1,3-glucanases (also known as $\alpha$-1,3-glucanohydrolases) which degrade the $\alpha$-1,3-glycosidic linkages in mutan. Mutanases have been described from two species of Trichoderma (Hasegawa et al., 1969, *Journal of Biological Chemistry* 244:5460– 5470; Guggenheim and Haller, 1972, *Journal of Dental Research* 51:394–402) and from a strain of Streptomyces (Takehara et al., 1981, *Journal of Bacteriology* 145:729–735). A mutanase gene from *Trichoderma harzianum* has been cloned and sequenced (Japanese Patent No. 4-58889/A).

Although mutanases have commercial potential for use as an antiplaque agent in dental applications and personal care products, e.g., toothpaste, chewing gum, or other oral and dental care products, the art has been unable to produce mutanases in significant quantities to be commercially useful.

It is an object of the present invention to provide new mutanases which can be produced in commercially useful quantities.

SUMMARY OF THE INVENTION

The present invention relates to isolated polypeptides having mutanase activity selected from the group consisting of:

(a) a polypeptide with an amino acid sequence set forth in SEQ ID NO:3;

(b) a polypeptide which is encoded by a nucleic acid sequence which is capable of hybridizing under high stringency conditions with (i) the nucleic acid sequence set forth in SEQ ID NO:2, or (ii) its complementary strand;

(c) a polypeptide with an amino acid sequence which has at least 60% identity with the amino acid sequence set forth in SEQ ID NO:3;

(d) an allelic form of (a), (b), or (c); and (e) a fragment of (a), (b), (c), or (d).

The present invention also relates to isolated nucleic acid sequences encoding the polypeptides and to nucleic acid constructs, vectors, and host cells comprising the nucleic acid sequences as well as methods for producing the polypeptides. The present invention further relates to oral cavity compositions and methods for degrading mutan.

BRIEF DESCRIPTION OF THE FIGURES

FIG. 3 shows the genomic DNA sequence and deduced amino acid sequence of *Penicillium purpurogenum* CBS 238.95 mutanase (SEQ ID NO:2 and SEQ ID NO:3, respectively).

FIG. 4 shows the alignment of the amino acid sequences for the *Penicillium purpurogenum* CBS 238.95 mutanase and the *Trichoderma harzianum* mutanase (SEQ ID NO:5).

DETAILED DESCRIPTION OF THE INVENTION

Polypeptides Having Mutanase Activity

Figure 1:
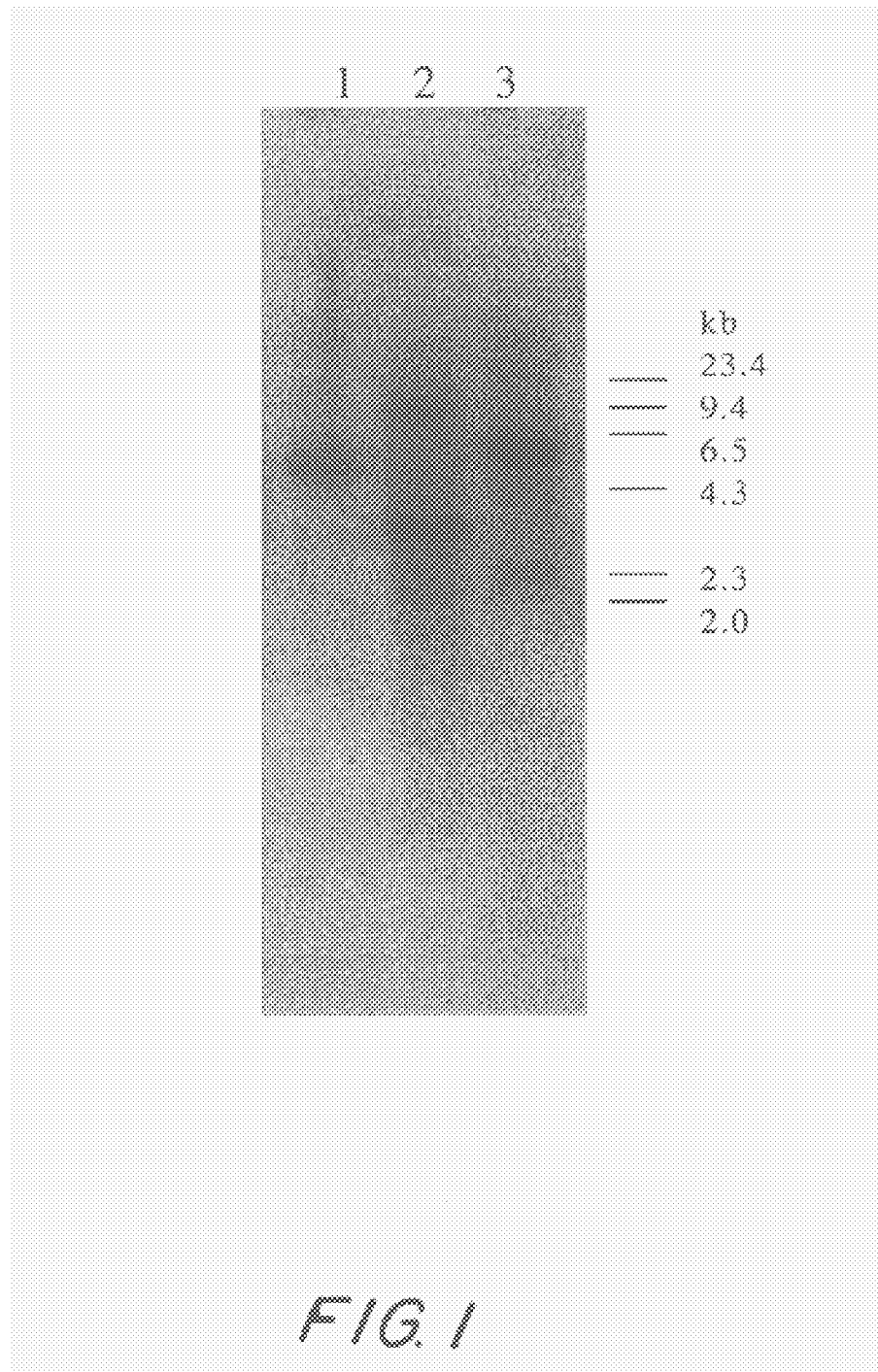
FIG. 1 shows the hybridization analysis of *Penicillium purpurogenum* genomic DNA with a *Trichoderma harzianum* cDNA probe.

In a first embodiment, the present invention relates to isolated polypeptides having mutanase activity with the amino acid sequence set forth in SEQ ID NO:3 or a fragment or subsequence thereof which retains mutanase activity. Preferably, a fragment contains at least 400 amino acid residues, more preferably at least 475 amino acid residues, even more preferably at least 550 amino acid residues, and most preferably at least 600 amino acid residues.

The polypeptides of the present invention are preferably obtained from species of Penicillium including, but not limited to, *Penicillium allahabadense, Penicillium arenicola, Penicillium asperum, Penicillium aurantiogriseum, Penicillium bilaii, Penicillium brevicompactum, Penicillium camembertii, Penicillium canescens, Penicillium chrysogenum, Penicillium citreonigrum, Penicillium citreoviride, Penicillium citrinum, Penicillium claviforme, Penicillium commune, Penicillium concentricum, Penicillium corylophilum, Penicillium corymbiferum, Penicillium crustosum, Penicillium cyclopium, Penicillium decumbens, Penicillium digitatum, Penicillium diversum, Penicillium duclauxii, Penicillium echinulatum, Penicillium expansum, Penicillium fellutanum, Penicillium frequentans, Penicillium funiculosum, Penicillium glabrum, Penicillium glandicola, Penicillium*

*granulatum, Penicillium griseofulvum, Penicillium hirsutum, Penicillium hordei, Penicillium implicatum, Penicillium islandicum, Penicillium italicum, Penicillium janczewskii, Penicillium janthinellum, Penicillium lividum, Penicillium luteum, Penicillium melinii, Penicillium miczynskii, Penicillium minioluteum, Penicillium montanense, Penicillium nigricans, Penicillium olivicolor, Penicillium olsonii, Penicillium oxalicum, Penicillium piceum, Penicillium pinophilum, Penicillium puberulum, Penicillium purpurogenum* (synonymous with *Penicillium rubrum*), *Penicillium pusillum, Penicillium raciborskii, Penicillium raistrickii, Penicillium restrictum, Penicillium roqueforti, Penicillium rugulosum, Penicillium sclerotiorum, Penicillium simplicissimum, Penicillium spiculisporum, Penicillium spinulosum, Penicillium stipitatum, Penicillium striatum, Penicillium terlikowskii, Penicillium thomii, Penicillium variabile, Penicillium vanians, Penicillium verniculatum, Penicillium verrucosum, Penicillium viridicatum, Penicillium vulpinum, Penicillium urticae, Penicillium waksmanii,* and *Penicillium wortmanni.* Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

In a more preferred embodiment, a polypeptide of the present invention is obtained from *Penicillium purpurogenum*, and most preferably from *Penicillium purpurogenum* CBS 238.95 or a mutant strain thereof, e.g., the polypeptide with the amino acid sequence set forth in SEQ ID NO:3.

A polypeptide of the present invention may also be obtained from teleomorphs of Penicillium, e.g., Eupenicillium and Talaromyces, including, but not limited to, *Eupenicillium alutaceum, Eupenicillium cinnamopurpureum, Eupenicillium crustaceum, Eupenicillium hirayamae, Eupenicillium pinetorum, Eupenicillium javanicum, Eupenicillium lapidosum, Eupenicillium ludwigii, Eupenicillium ochrosalmoneum, Eupenicillium shearii, Talaromyces flavus, Talaromyces stipitatus, Talaromyces luteus, Talaromyces wortmanii, Talaromyces trachyspermus, Talaromyces thermophilus,* and *Talaromnyces striatus.*

A polypeptide of the present invention may further be obtained from other fungi which are synonyms of Penicillium as defined by Samson and Pitt In Samson and Pitt (eds.), *Advances in Penicillium and Aspergillus Systematics,* Plenum Press, ASI Series, New York, 1985. Penicillium is a genus of Hyphomycetes, characterized by the production of conidia, which are usually green, in chains from verticils of phialides. Phialides may be directly supported on a stipe or on one, two, or rarely three compact stages of supporting cells: metulae and rami in that order, with ramuli in between on occasion. Phialides have short straight necks and smooth walls, and are characteristically produced on a stipe or a metula over a period of time, not simultaneously.

For purposes of the present invention, the term "obtained from" as used herein in connection with a given source shall mean that the polypeptide is produced by the source or by a cell in which a gene from the source has been inserted.

In a second embodiment, the present invention relates to polypeptides which are encoded by nucleic acid sequences which are capable of hybridizing under high stringency conditions with an oligonucleotide probe which hybridizes under the same conditions with the nucleic acid sequence set forth in SEQ ID NO:2 or its complementary strand (J. Sambrook, E. F. Fritsch, and T. Maniatus, 1989, *Molecular Cloning, A Laboratory Manual,* 2d edition, Cold Spring Harbor, N.Y.). Hybridization indicates that the analogous nucleic acid sequence hybridizes to the oligonucleotide probe corresponding to the polypeptide encoding part of the nucleic acid sequence shown in SEQ ID NO:2, under low to high stringency conditions (for example, prehybridization and hybridization at 42° C. in 5× SSPE, 0.3% SDS, 200 μg/ml sheared and denatured salmon sperm DNA, and either 50, 35 or 25% formamide for high, medium and low stringencies, respectively), following standard Southern blotting procedures.

SEQ ID NO:2 may be used to identify and clone DNA encoding polypeptides having mutanase activity from other strains of different genera or species according to methods well known in the art. Thus, a genomic, cDNA or combinatorial chemical library prepared from such other organisms may be screened for DNA which hybridizes with SEQ ID NO:2 and encodes mutanase. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify clones or DNA which is homologous with SEQ ID NO:2, the carrier material is used in a Southern blot in which the carrier material is finally washed three times for 30 minutes each using 2×SSC, 0.2% SDS at preferably not higher than 50° C., more preferably not higher than 55° C., more preferably not higher than 60° C., and even more preferably not higher than 65° C. Molecules to which the oligonucleotide probe hybridizes under these conditions are detected using X-ray film.

In a third embodiment, the present invention relates to polypeptides which have an amino acid sequence which has a degree of identity to the amino acid sequence set forth in SEQ ID NO:3 of at least about 60%, preferably at least about 70%, more preferably at least about 80%, even more preferably at least about 90%, most preferably at least 95%, and even most preferably at least about 97%, which qualitatively retain the mutanase activity of the polypeptides (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from the amino acid sequence set forth in SEQ ID NO:3. The degree of identity between two or more amino acid sequences may be determined by means of computer programs known in the art such as GAP provided in the GCG program package (Needleman and Wunsch, 1970, *Journal of Molecular Biology* 48:443–453). For purposes of determining the degree of identity between two amino acid sequences for the present invention, the Clustal method (Higgins, 1989, *CABIOS* 5: 151–153) is used with an identity table, a gap penalty of 10, and a gap length of 10.

The amino acid sequences of the homologous polypeptides differ from the amino acid sequence set forth in SEQ ID NO:3 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (such as arginine, lysine and histidine), acidic amino acids (such as glutamic acid and aspartic acid), polar amino acids (such as glutamine and asparagine), hydrophobic amino acids (such as leucine, isoleucine and valine), aromatic amino acids (such as phenylalanine, tryptophan and tyrosine), and small amino acids (such as glycine, alanine, serine, threonine and methionine). Amino acid substitutions which do not generally alter the specific activity are known in the art and are described, e.g., by H. Neurath and R. L. Hill, 1979, In, The Proteins, Academic Press, New York. The most commonly occurring exchanges are: Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/Gly as well as these in reverse.

The present invention also relates to polypeptides having immunochemical identity or partial immunochemical identity to the polypeptide native to *Penicillium purpurogenum* CBS 238.95. In this embodiment, a polypeptide of the present invention is used to produce antibodies which are immunoreactive or bind to epitopes of the polypeptide. A polypeptide having immunochemical identity to the polypeptide native to *Penicillium purpurogenum* CBS 238.95 means that an antiserum containing antibodies against the polypeptide native to *Penicillium purpurogenum* CBS 238.95 reacts with the other polypeptide in an identical fashion such as total fusion of precipitates, identical precipitate morphology, and/or identical electrophoretic mobility using a specific immunochemical technique. A further explanation of immunochemical identity is described by Axelsen, Bock, and Krøll, In N. H. Axelsen, J. Krøll, and B. Weeks, editors, *A Manual of Quantitative Immunoelectrophoresis*, Blackwell Scientific Publications, 1973, Chapter 10. Partial inumunochemical identity means that an antiserum containing antibodies against the polypeptide native to *Penicillium purpurogenum* CBS 238.95 reacts with the other polypeptide in a partially identical fashion such as partial fusion of precipitates, partially identical precipitate morphology, and/or partially identical electrophoretic mobility using a specific immunochemical technique. A further explanation of partial immunochemical identity is described by Bock and Axelsen, In N. H. Axelsen, J. Krøll, and B. Weeks, editors, *A Manual of Quantitative Immunoelectrophoresis*, Blackwell Scientific Publications, 1973, Chapter 11. The immunochemical properties are determined by immunological cross-reaction identity tests by the well-known Ouchterlony double immunodiffusion procedure. Specifically, an antiserum against the polypeptide of the invention is raised by immunizing rabbits (or other rodents) according to the procedure described by Harboe and Ingild, In N. H. Axelsen, J. Krøll, and B. Weeks, editors, *A Manual of Quantitative Immunoelectrophoresis*, Blackwell Scientific Publications, 1973, Chapter 23, or Johnstone and Thorpe, *Immunochemistry in Practice*, Blackwell Scientific Publications, 1982 (more specifically pages 27–31).

Polypeptides which are encoded by nucleic acid sequences which are capable of hybridizing with an oligonucleotide probe which hybridizes with the nucleic acid sequence set forth in SEQ ID NO:2, its complementary strand or a subsequence thereof, the homologous polypeptides and polypeptides having identical or partially identical immunological properties may be obtained from microorganisms of any genus, preferably from a bacterial or fungal source. Sources for such polypeptides are strains of the genus Penicillium and species thereof available in public depositories. Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a cDNA library of another microorganism, in particular a fungus, such as a strain of an Aspergillus sp., in particular a strain of *Aspergillus aculeatus, Aspergillus awamori, Aspergillus foetidus, Aspergillus japonicus, Aspergillus nidulans, Aspergillus niger* or *Aspergillus oryzae*, a strain of Trichoderma sp., in particular a strain of *Trichoderma harzianum, Trichoderma koningii, Trichoderma longibrachiatum, Trichoderma reesei* or *Trichoderma viride,* or a strain of a Fusarium sp., in particular a strain of *Fusarium cerealis, Fusarium crookwellense, Fusarium graminearum, Fusarium oxysporum, Fusarium sambucinum* or *Fusarium sulphureum,* or a strain of a Humicola sp., or a strain of an Aureobasidium sp., a Cryptococcus sp., a Filibasidium sp., a Magnaporthe sp., a Myceliophthora sp., a Neocallimastix sp., a Paecilomyces sp., a Piromyces sp., a Talaromyces sp., a Thermoascus sp., a Thielavia sp., or a Schizophyllum sp. Once a nucleic acid sequence encoding a polypeptide has been detected with the probe(s), the sequence may be isolated or cloned by utilizing techniques which are known to those of ordinary skill in the art (see, e.g., Sambrook et al., supra).

As defined herein, an "isolated" polypeptide is a polypeptide which is essentially free of other non-mutanase polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

The present invention also relates to hybrid or fusion polypeptides, comprising the catalytic domain included in the amino acid sequence set forth in SEQ ID NO:3. In a preferred embodiment, these polypeptides have mutanase activity.

The present invention also relates to hybrid or fusion polypeptides, comprising the linker included in the amino acid sequence set forth in SEQ ID NO:3. In a preferred embodiment, these polypeptides have mutanase activity.

The present invention also relates to hybrid or fusion polypeptides, comprising the mutan binding domain included in the amino acid sequence set forth in SEQ ID NO:3. In a preferred embodiment, these polypeptides have mutanase activity.

Nucleic Acid Sequences

The present invention also relates to isolated nucleic acid sequences which encode a polypeptide of the present invention. In a preferred embodiment, the nucleic acid sequence encodes a polypeptide obtained from Penicillium, e.g., *Penicillium purpurogenum*, and in a more preferred embodiment, the nucleic acid sequence is obtained from *Penicillium purpurogenum* CBS 238.95, e.g., the nucleic acid sequence set forth in SEQ ID NO:2. In a more preferred embodiment, the nucleic acid sequence is the sequence contained in plasmid pZL-Pp6A which is contained in *Escherichia coli* NRRL B-21518. The present invention also encompasses nucleic acid sequences which encode a polypeptide having the amino acid sequence set forth in SEQ ID NO:3, which differ from SEQ ID NO:2 by virtue of the degeneracy of the genetic code. The present invention also relates to subsequences of SEQ ID NO:2 which encode a fragment of SEQ ID NO:3 which retains mutanase activity. Preferably, a subsequence of SEQ ID NO:2 which encodes a fragment of SEQ ID NO:3 which retains mutanase activity contains at least 1400 nucleotides, more preferably at least 1650 nucleotides, and most preferably at least 1800 nucleotides.

As described above, the nucleic acid sequences may be obtained from microorganisms which are synonyms or teleomorphs of Penicillium as defined by Samson and Pitt, 1985, supra.

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *A Guide to Methods and Application,* Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of the Penicillium producing the polypeptide, or another or related organism and thus, for example, may be an allelic or species variant of the polypeptide encoding region of the nucleic acid sequence.

The term "isolated" nucleic acid sequence as used herein refers to a nucleic acid sequence which is essentially free of other nucleic acid sequences, e.g., at least about 20% pure, preferably at least about 40% pure, more preferably about 60% pure, even more preferably about 80% pure, most preferably about 90% pure, and even most preferably about 95% pure, as determined by agarose gel electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The present invention also relates to nucleic acid sequences which have a nucleic acid sequence which has a degree of identity to the nucleic acid sequence set forth in SEQ ID NO:2 of at least about 60%, preferably at least about 70%, more preferably at least about 80%, even more preferably at least about 90%, most preferably at least about 95%, and even most preferably at least about 97%, which encode an active polypeptide. The degree of identity between two nucleic acid sequences may be determined by means of computer programs known in the art such as GAP provided in the GCG program package (Needleman and Wunsch, 1970, *Journal of Molecular Biology* 48:443–453). For purposes of determining the degree of identity between two nucleic acid sequences for the present invention, the Clustal method (Higgins, 1989, supra) is used with an identity table, a gap penalty of 10, and a gap length of 10.

Modification of the nucleic acid sequence encoding the polypeptide may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source. For example, it may be of interest to synthesize variants of the polypeptide where the variants differ in specific activity, thermostability, pH optimum, or the like using, e.g., site-directed mutagenesis. The analogous sequence may be constructed on the basis of the nucleic acid sequence presented as the polypeptide encoding part of SEQ ID NO:2, e.g., a sub-sequence thereof, and/or by introduction of nucleotide substitutions which do not give rise to another amino acid sequence of the polypeptide encoded by the nucleic acid sequence, but which corresponds to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2:95–107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244:1081–1085). In the latter technique mutations are introduced at every residue in the molecule, and the resultant mutant molecules are tested for mutanase activity to identify amino acid residues that are critical to the activity of the molecule. Sites of substrate-enzyme interaction can also be determined by analysis of three-dimensional structure as determined by such techniques as nuclear magnetic resonance analysis, crystallography or photoaffinity labelling (see, e.g., de Vos et al., 1992, *Science* 255, 306–312; Smith et al., 1992, *Journal of Molecular Biology* 224:899–904; Wlodaver et al., 1992, *FEBS Letters* 309, 59–64).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include, ligating the coding sequences encoding the polypeptides so that they are in frame and that expression of the fused polypeptide is under control of the same promoter(s) and terminator.

The present invention also relates to nucleic acid sequences which are capable of hybridizing under high stringency conditions with an oligonucleotide probe which hybridizes under the same conditions with the nucleic acid sequence set forth in SEQ ID NO:2 or its complementary strand (Sambrook et al., supra). Hybridization indicates that the analogous nucleic acid sequence hybridizes to the oligonucleotide probe corresponding to the polypeptide encoding part of the nucleic acid sequence shown in SEQ ID NO:2 under standard conditions.

The amino acid sequence set forth in SEQ ID NO:3 or a partial amino acid sequence thereof may be used to design an oligonucleotide probe, or a gene encoding a polypeptide of the present invention or a subsequence thereof can also be used as a probe, to isolate homologous genes of any genus or species. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 40 nucleotides in length. Longer probes can also be used. Both DNA and RNA probes can be used. The probes are typically labeled for detecting the corresponding gene (for example, with $^{32}$P, $^{3}$H, $^{35}$S, biotin, or avidin). A PCR reaction using the degenerate probes mentioned herein and genomic DNA or first-strand cDNA from a *Penicillium purpurogenum* strain can also yield a *Penicillium purpurogenum* mutanase-specific product which can then be used as a probe to clone the corresponding genomic or cDNA.

Nucleic Acid Constructs

The present invention also relates to nucleic acid constructs comprising a nucleic acid sequence of the present invention operably linked to one or more control sequences capable of directing the expression of the coding sequence in a suitable host cell under conditions compatible with the control sequences.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct may be synonymous with the term expression cassette when the nucleic acid construct contains all the control sequences required for expression of a coding sequence of the present invention. The term "coding sequence" as defined herein is a sequence which is transcribed into mRNA and translated into a polypeptide of the present invention when placed under the control of the above mentioned control sequences. The boundaries of the coding sequence are generally determined by a translation start codon ATG at the 5'-terminus and a translation stop codon at the 3'-terminus. A coding sequence can include, but is not limited to, genomic DNA, cDNA, and recombinant nucleic acid sequences.

An isolated nucleic acid sequence encoding a polypeptide of the present invention may be manipulated in a variety of ways to provide for expression of the polypeptide. Manipulation of the nucleic acid sequence encoding a polypeptide prior to its insertion into a vector may be desirable or necessary depending on the expression vector. The techniques for modifying nucleic acid sequences utilizing cloning methods are well known in the art.

The term "control sequences" is defined herein to include all components which are necessary or advantageous for expression of the coding sequence of the nucleic acid sequence. Each control sequence may be native or foreign to the nucleic acid sequence encoding the polypeptide. Such control sequences include, but are not limited to, a leader, a polyadenylation sequence, a propeptide sequence, a promoter, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

The control sequence may be an appropriate promoter sequence, a nucleic acid sequence which is recognized by a host cell for expression of the nucleic acid sequence. The promoter sequence contains transcription control sequences which mediate the expression of the polypeptide. The promoter may be any nucleic acid sequence which shows transcriptional activity in the host cell of choice and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, the *Streptomyces coelicolor* agarase gene (dagA), the *Bacillus subtilis* levansucrase gene (sacB), the *Bacillus licheniformis* alpha-amylase gene (amyL), the *Bacillus stearothermophilus* maltogenic amylase gene (amyM), the *Bacillus amyloliquefaciens* alpha-amylase gene (amyQ), the *Bacillus licheniformis* penicillinase gene (penP), the *Bacillus subtilis* xylA and xylB genes, and the prokaryotic beta-lactamase gene (Villa-Kamaroff et al., 1978, *Proceedings of the National Academy of Sciences USA* 75:3727–3731), as well as the tac promoter (DeBoer et al., 1983, *Proceedings of the National Academy of Sciences USA* 80:21–25). Further promoters are described in "Useful proteins from recombinant bacteria" in *Scientific American*, 1980, 242:74–94; and in Sambrook et al., 1989, supra.

Examples of suitable promoters for directing the transcription of the nucleic acid constructs of the present invention in a filamentous fungal host cell are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (as described in U.S. Pat. No. 4,288,627, which is incorporated herein by reference), and hybrids thereof. Particularly preferred promoters for use in filamentous fungal host cells are the TAKA amylase, NA2-tpi (a hybrid of the promoters from the genes encoding *Aspergillus niger* neutral a-amylase and *Aspergillus oryzae* triose phosphate isomerase), and glaA promoters.

In a yeast host, useful promoters are obtained from the *Saccharomyces cerevisiae* enolase (ENO-1) gene, the *Saccharomyces cerevisiae* galactokinase gene (GAL1), the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, *Yeast* 8:423–488. In a mammalian host cell, useful promoters include viral promoters such as those from Simian Virus 40 (SV40), Rous sarcoma virus (RSV), adenovirus, and bovine papilloma virus (BPV).

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fungal host cells are obtained from the genes encoding *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes encoding *Saccharomyces cerevisiae* enolase,

*Saccharomyces cerevisiae* cytochrome C (CYC1), or *Saccharomyces cerevisiae* glyceraldehyde-3-phosphate dehydrogenase. Other useful terminators for yeast host cells are described by Romanos et al., 1992, supra. Terminator sequences are well known in the art for mammalian host cells.

The control sequence may also be a suitable leader sequence, a nontranslated region of a mRNA which is important for translation by the host cell. The leader sequence is operably linked to the 5' terminus of the nucleic acid sequence encoding the polypeptide. Any leader sequence which is functional in the host cell of choice may be used in the present invention.

Preferred leaders for filamentous fungal host cells are obtained from the genes encoding *Aspergillus oryzae* TAKA amylase and *Aspergillus oryzae* triose phosphate isomerase.

Suitable leaders for yeast host cells are obtained from the *Saccharomyces cerevisiae* enolase (ENO-1) gene, the *Saccharomyces cerevisiae* 3-phosphoglycerate kinase gene, the *Saccharomyces cerevisiae* alpha-factor, and the *Saccharomyces cerevisiae* alcohol dehydrogenase/glyceraldehyde-3-phosphate dehydrogenase genes (ADH2/GAP).

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes encoding *Aspergillus oryzae* TAKA amylase, *Aspergillus niger* glucoamylase, *Aspergillus nidulans* anthranilate synthase, and *Aspergillus niger* alpha-glucosidase.

Useful polyadenylation sequences for yeast host cells are described by Guo and Sherman, 1995, *Molecular Cellular Biology* 15:5983–5990. Polyadenylation sequences are well known in the art for mammalian host cells.

The control sequence may also be a signal peptide coding region, which codes for an amino acid sequence linked to the amino terminus of the polypeptide which can direct the expressed polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to that portion of the coding sequence which encodes the secreted polypeptide. The foreign signal peptide coding region may be required where the coding sequence does not normally contain a signal peptide coding region. Alternatively, the foreign signal peptide coding region may simply replace the natural signal peptide coding region in order to obtain enhanced secretion of the mutanase relative to the natural signal peptide coding region normally associated with the coding sequence. The signal peptide coding region may be obtained from a glucoamylase or an amylase gene from an Aspergillus species, a lipase or proteinase gene from a Rhizomucor species, the gene for the alpha-factor from *Saccharomyces cerevisiae*, an amylase or a protease gene from a Bacillus species, or the calf preprochymosin gene. However, any signal peptide coding region capable of directing the expressed mutanase into the secretory pathway of a host cell of choice may be used in the present invention.

An effective signal peptide coding region for bacterial host cells is the signal peptide coding region obtained from the maltogenic amylase gene from Bacillus NCIB 11837, the *Bacillus stearothermophilus* alpha-amylase gene, the *Bacillus licheniformis* subtilisin gene, the *Bacillus licheniformis* beta-lactamase gene, the *Bacillus stearothermophilus* neutral proteases genes (nprT, nprS, nprM), and the *Bacillus subtilis* PrsA gene. Further signal peptides are described by Simonen and Palva, 1993, *Microbiological Reviews* 57:109–137.

An effective signal peptide coding region for filamentous fungal host cells is the signal peptide coding region obtained from *Aspergillus oryzae* TAKA amylase gene, *Aspergillus niger* neutral amylase gene, the *Rhizomucor miehei* aspartic proteinase gene, the *Humicola lanuginosa* cellulase gene, or the *Rhizomucor miehei* lipase gene.

Useful signal peptides for yeast host cells are obtained from the genes for *Saccharomyces cerevisiae* a-factor and *Saccharomyces cerevisiae* invertase. Other useful signal peptide coding regions are described by Romanos et al., 1992, supra.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to mature active polypeptide by catalytic or autocatalytic cleavage of the propeptide from the propolypeptide. The propeptide coding region may be obtained from the *Bacillus subtilis* alkaline protease gene (aprE), the *Bacillus subtilis* neutral protease gene (nprT), the *Saccharomyces cerevisiae* alpha-factor gene, or the *Myceliophthora thermophilum* laccase gene (WO 95/33836).

The nucleic acid constructs of the present invention may also comprise one or more nucleic acid sequences which encode one or more factors that are advantageous in the expression of the polypeptide, e.g., an activator (e.g., a trans-acting factor), a chaperone, and a processing protease. Any factor that is functional in the host cell of choice may be used in the present invention. The nucleic acids encoding one or more of these factors are not necessarily in tandem with the nucleic acid sequence encoding the polypeptide.

An activator is a protein which activates transcription of a nucleic acid sequence encoding a polypeptide (Kudla et al., 1990, *EMBO Journal* 9:1355–1364; Jarai and Buxton, 1994, *Current Genetics* 26:2238–244; Verdier, 1990, *Yeast* 6:271–297). The nucleic acid sequence encoding an activator may be obtained from the genes encoding *Bacillus stearothermophilus* NprA (nprA), *Saccharomyces cerevisiae* heme activator protein 1 (hap1), *Saccharomyces cerevisiae* galactose metabolizing protein 4 (gal4), and *Aspergillus nidulans* ammonia regulation protein (areA). For further examples, see Verdier, 1990, supra and MacKenzie et al., 1993, *Journal of General Microbiology* 139:2295–2307.

A chaperone is a protein which assists another polypeptide in folding properly (Hartl et al., 1994, *TIBS* 19:20–25; Bergeron et al., 1994, *TIBS* 19:124–128; Demolder et al., 1994, *Journal of Biotechnology* 32:179–189; Craig, 1993, *Science* 260:1902–1903; Gething and Sambrook, 1992, *Nature* 355:33–45; Puig and Gilbert, 1994, *Journal of Biological Chemistry* 269:7764–7771; Wang and Tsou, 1993, *The FASEB Journal* 7:1515–11157; Robinson et al., 1994, *Bio/Technology* 1:381–384). The nucleic acid sequence encoding a chaperone may be obtained from the genes encoding *Bacillus subtilis* GroE proteins, *Aspergillus oryzae* protein disulphide isomerase, *Saccharomyces cerevisiae* calnexin, *Saccharomyces cerevisiae* BiP/GRP78, and *Saccharomyces cerevisiae* Hsp70. For farther examples, see Gething and Sambrook, 1992, supra, and Hartl et al., 1994, supra.

A processing protease is a protease that cleaves a propeptide to generate a mature biochemically active polypeptide (Enderlin and Ogrydziak, 1994, Yeast 10:67–79; Fuller et al., 1989, *Proceedings of the National Academy of Sciences USA* 86:1434–1438; Julius et al., 1984, *Cell* 37:1075–1089; Julius et al., 1983, *Cell* 32:839–852). The nucleic acid sequence encoding a processing protease may be obtained from the genes encoding *Saccharomyces cerevisiae* dipeptidylaminopeptidase, *Saccharomyces cerevisiae* Kex2, and *Yarrowia lipolytica* dibasic processing endoprotease (xpr6).

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. In yeast, the ADH2 system or GAL1 system may be used. In filamentous fungi, the TAKA alpha-amylase promoter, *Aspergillus niger* glucoamylase promoter, and the *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be placed in tandem with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression, and possibly secretion.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids. The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when is introduced into the host cell, is integrated into the genome and replicated together with the chromosome(s) into which it has been integrated. The vector system may be a single vector or plasmid or two or more vectors or plasmids which together contain the total DNA to be introduced into the genome of the host cell, or a transposon.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. A frequently used mammalian marker is the dihydrofolate reductase gene. Suitable markers for yeast host cells are ADE2, HIS3, LEU2, LYS2, MET3, TRP1, and URA3. A selectable marker for use in a filamentous fungal host cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), and glufosinate resistance markers, as well as equivalents from other species. Preferred for use in an Aspergillus cell are the amdS and pyrG markers of *Aspergillus nidulans* or *Aspergillus oryzae* and the bar marker of *Streptomyces hygroscopicus*. Furthermore, selection may be accomplished by co-transformation, e.g., as described in WO 91/17243, where the selectable marker is on a separate vector.

The vectors of the present invention preferably contain an element(s) that permits stable integration of the vector into the host cell genome or autonomous replication of the vector in the cell independent of the genome of the cell.

The vectors of the present invention may be integrated into the host cell genome when introduced into a host cell. For integration, the vector may rely on the nucleic acid sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination. These nucleic acid sequences may be any sequence that is homologous with a target sequence in the genome of the host cell, and, furthermore, may be non-encoding or encoding sequences.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in Bacillus. Examples of origin of replications for use in a yeast host cell are the 2 micron origin of replication, the combination of CEN6 and ARS4, and the combination of CEN3 and ARS1. The origin of replication may be one having a mutation which makes its functioning temperature-sensitive in the host cell (see, e.g., Ehrlich, 1978, *Proceedings of the National Academy of Sciences USA* 75:1433).

More than one copy of a nucleic acid sequence encoding a polypeptide of the present invention may be inserted into the host cell to amplify expression of the nucleic acid sequence. Stable amplification of the nucleic acid sequence can be obtained by integrating at least one additional copy of the sequence into the host cell genome using methods well known in the art and selecting for transformants.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. The term "host cell" encompasses any progeny of a parent cell which is not identical to the parent cell due to mutations that occur during replication.

The cell is preferably transformed with a vector comprising a nucleic acid sequence of the invention followed by integration of the vector into the host chromosome. "Transformation" means introducing a vector comprising a nucleic acid sequence of the present invention into a host cell so that the vector is maintained as a chromosomal integrant or as a self-replicating extra-chromosomal vector. Integration is generally considered to be an advantage as the nucleic acid sequence is more likely to be stably maintained in the cell. Integration of the vector into the host chromosome may occur by homologous or non-homologous recombination as described above.

The choice of a host cell will to a large extent depend upon the gene encoding the polypeptide and its source. The host cell may be a unicellular microorganism, e.g., a prokaryote, or a non-unicellular microorganism, e.g., a eukaryote. Useful unicellular cells are bacterial cells such as gram positive bacteria including, but not limited to, a Bacillus cell, e.g., *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis,* and *Bacillus thuringiensis;* or a Streptomyces cell, e.g., *Streptomyces lividans* or *Streptomyces murinus,* or gram negative bacteria such as *E. coli* and Pseudomonas sp. In a preferred embodiment, the bacterial host cell is a *Bacillus lentus, Bacillus licheniformis, Bacillus stearothermophilus* or *Bacillus subtilis* cell. The transformation of a bacterial host cell may, for instance, be effected by protoplast transformation (see, e.g., Chang and Cohen, 1979, *Molecular General Genetics* 168:111–115), by using competent cells (see, e.g., Young and Spizizin, 1961, *Journal of Bacteriology* 81:823–829, or Dubnar and Davidoff-Abelson, 1971, *Journal of Molecular Biology* 56:209–221), by electroporation (see, e.g., Shigekawa and Dower, 1988, *Biotechniques* 6:742–751), or by conjugation (see, e.g., Koehler and Thorne, 1987, *Journal of Bacteriology* 169:5771–5278).

The host cell may be a eukaryote, such as a mammalian cell, an insect cell, a plant cell or a fungal cell. Useful mammalian cells include Chinese hamster ovary (CHO) cells, HeLa cells, baby hamster kidney (BHK) cells, COS cells, or any number of other immortalized cell lines available, e.g., from the American Type Culture Collection.

In a preferred embodiment, the host cell is a fungal cell. "Fungi" as used herein includes the phyla Ascomycota, Basidiomycota, Chytridiomycota, and Zygomycota (as defined by Hawksworth et al., *In, Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra). Representative groups of Ascomycota include, e.g., Neurospora, Eupenicillium (=Penicillium), Emericella (=Aspergillus), Eurotium (=Aspergillus), and the true yeasts listed above. Examples of Basidiomycota include mushrooms, rusts, and smuts. Representative groups of Chytridiomycota include, e.g., Allomyces, Blastocladiella, Coelomomyces, and aquatic fungi. Representative groups of Oomycota include, e.g., Saprolegniomycetous aquatic fungi (water molds) such as Achlya. Examples of mitosporic fungi include Aspergillus, Penicillium, Candida, and Alternaria. Representative groups of Zygomycota include, e.g., Rhizopus and Mucor.

In a preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). The ascosporogenous yeasts are divided into the families Spermophthoraceae and Saccharomycetaceae. The latter is comprised of four subfamilies, Schizosaccharomycoideae (e.g., genus Schizosaccharomyces), Nadsonioideae, Lipomycoideae, and Saccharomycoideae (e.g., genera Pichia, Kluyveromyces and Saccharomyces). The basidiosporogenous yeasts include the genera Leucosporidim, Rhodosporidium, Sporidiobolus, Filobasidium, and Filobasidiella. Yeast belonging to the Fungi Imperfecti are divided into two families, Sporobolomycetaceae (e.g., genera Sorobolomyces and Bullera) and Cryptococcaceae (e.g., genus Candida). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980. The biology of yeast and manipulation of yeast genetics are well known in the art (see, e.g., *Biochemistry and Genetics of Yeast,* Bacil, M., Horecker, B. J., and Stopani, A. O. M., editors, 2nd edition, 1987; *The Yeasts,* Rose, A. H., and Harrison, J. S., editors, 2nd edition, 1987; and *The Molecular Biology of the Yeast Saccharomyces,* Strathern et al., editors, 1981).

In a more preferred embodiment, the yeast host cell is a cell of a species of Candida, Kluyveromyces, Saccharomyces, Schizosaccharomyces, Pichia, or Yarrowia.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In a preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a vegetative mycelium composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative. In a more preferred embodiment, the filamentous fungal host cell is a cell of a species of, but not limited to, Acremonium, Aspergillus, Fusarium, Humicola, Mucor, Myceliophthora, Neurospora, Penicillium, Thielavia, Tolypocladium, and Trichoderma.

In an even more preferred embodiment, the filamentous fungal host cell is an Aspergillus cell. In another even more preferred embodiment, the filamentous fungal host cell is an Acremonium cell. In another even more preferred embodiment, the filamentous fungal host cell is a Fusarium cell. In another even more preferred embodiment, the filamentous fungal host cell is a Humicola cell. In another even more preferred embodiment, the filamentous fungal host cell is a Mucor cell. In another even more preferred embodiment, the filamentous fungal host cell is a Myceliophthora cell. In another even more preferred embodiment, the filamentous fungal host cell is a Neurospora cell. In another even more preferred embodiment, the filamentous fungal host cell is a Penicillium cell. In another even more preferred embodiment, the filamentous fungal host cell is a Thielavia cell. In another even more preferred embodiment, the filamentous fungal host cell is a Tolypocladium cell. In another even more preferred embodiment, the filamentous fungal host cell is a Trichoderma cell.

In a most preferred embodiment, the filamentous fungal host cell is an *Aspergillus awamori, Aspergillus foetidus, Aspergillus japonicus, Aspergillus niger* or *Aspergillus oryzae* cell. In another most preferred embodiment, the filamentous fungal host cell is a *Fusarium cerealis, Fusarium crookwellense, Fusarium graminearum, Fusarium oxysporum, Fusarium sambucinum* or *Fusarium sulphureum* cell. In another most preferred embodiment, the filamentous fungal host cell is a *Humicola insolens* or *Humicola lanuginosa* cell. In another most preferred embodiment, the filamentous fungal host cell is a *Mucor miehei* cell. In another most preferred embodiment, the filamentous fungal host cell is a *Myceliophthora thermophilum* cell. In another most preferred embodiment, the filamentous fungal host cell is a *Neurospora crassa* cell. In another most preferred embodiment, the filamentous fungal host cell is a *Penicillium purpurogenum* cell. In another most preferred embodiment, the filamentous fungal host cell is a *Thielavia terrestris* cell. In another most preferred embodiment, the Trichoderma cell is a *Trichoderma harzianum, Trichoderma koningii, Trichoderma longibrachiatum, Trichoderma reesei* or *Trichoderma viride* cell.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, *Proceedings of the National Academy of Sciences USA* 81:1470–1474. A suitable method of transforming Fusarium species is described by Malardier et al., 1989, *Gene* 78:147–156 or in copending U.S. Ser. No. 08/269,449. Yeast may be transformed using the procedures described by Becker and Guarente, In Abelson, J. N. and Simon, M. I., editors, *Guide to Yeast Genetics and Molecular Biology,* Methods in Enzymology, Volume 194, pp 182–187, Academic Press, Inc., New York; Ito et al., 1983, *Journal of Bacteriology* 153:163; and Hinnen et al., 1978, *Proceedings of the National Academy of Sciences USA* 75:1920. Mammalian cells may be transformed by direct uptake using the calcium phosphate precipitation method of Graham and Van der Eb (1978, *Virology* 52:546).

Methods of Production

The present invention also relates to methods for producing a polypeptide of the present invention comprising (a) cultivating a Penicillium strain to produce a supernatant comprising the polypeptide; and (b) recovering the polypeptide.

The present invention also relates to methods for producing a polypeptide of the present invention comprising (a) cultivating a host cell under conditions conducive to expression of the polypeptide; and (b) recovering the polypeptide.

In both methods, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art (see, e.g., references for bacteria and yeast; Bennett, J. W. and LaSure, L., editors, *More Gene Manipulations in Fungi,* Academic Press, California, 1991). Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it is recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide. Procedures for determining mutanase activity are known in the art and include, e.g., high performance size exclusion chromatography of mutanase-digested mutan.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation. The recovered polypeptide may then be further purified by a variety of chromatographic procedures, e.g., ion exchange chromatography, gel filtration chromatography, affinity chromatography, or the like.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., *Protein Purfication,* J.-C. Janson and Lars Ryden, editors, VCH Publishers, New York, 1989).

Polypeptide Compositions

In a still further aspect, the present invention relates to polypeptide compositions which are enriched in a polypeptide of the present invention. In the present context, the term "enriched" is intended to indicate that the mutanase activity of the polypeptide composition has been increased, e.g., with an enrichment factor of 1.1, conveniently due to addition of a polypeptide of the invention.

The polypeptide composition may be one which comprises a polypeptide of the invention as the major enzymatic component, e.g., a mono-component polypeptide composition. Alternatively, the composition may comprise multiple enzymatic activities, such as an aminopeptidase, an amylase, a carbohydrase, a carboxypeptidase, a catalase, a cellulase, a chitinase, a cutinase, a deoxyribonuclease, an esterase, an alpha-galactosidase, a beta-galactosidase, a glucoamylase, an alpha-glucosidase, a beta-glucosidase, a haloperoxidase, an invertase, a laccase, a lipase, a mannosidase, a mutanase, an oxidase, a pectinolytic enzyme, a peroxidase, a phytase, a polyphenoloxidase, a proteolytic enzyme, a ribonuclease, or a xylanase. The additional enzyme(s) may be producible by means of a microorganism belonging to the genus Aspergillus, preferably *Aspergillus aculeatus, Aspergillus awamori, Aspergillus niger,* or *Aspergillus oryzae,* or Trichoderma, Humicola, preferably *Humicola insolens,* or Fusarium, preferably *Fusarium graminearum.*

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The mutanase of the present invention can be used as an antiplaque agent to degrade mutan produced by *Streptococcus mutans* in the oral cavity (Guggenheim, 1970, *Helv. Odont. Acta* 14:89–108). Mutan plays an important role for adhesion and proliferation of bacteria on the surface of teeth and, hence, may be important in the etiology of dental caries (Kelstrup, 1978, *Danish Dental Journal* 82:431–437).

The present invention is also directed to oral cavity compositions, particularly dentifrices, comprising the mutanase in an effective amount and a suitable oral carrier for use as an antiplaque agent in dental applications and personal care products. "Effective amount" is defined herein as a sufficient amount of the mutanase to reduce plaque. "Suitable oral carrier" is defined herein as a suitable vehicle which can be used to apply the compositions of the present invention to the oral cavity in a safe and effective manner. The compositions of the present invention can be made using methods which are common in the oral product area. Dentifrices are compositions used in conjunction with a toothbrush to remove stains from teeth and to leave the mouth feeling clean and refreshed after brushing. Dentifrices are also used to deliver agents with specific therapeutic and cosmetic functions. Examples of personal care products include, but are not limited to, toothpaste, toothgel, mouthwash, chewing gum, and denture cleaners.

The composition ingredients will vary depending on the particular product (Kirk-Othmer, John Wiley & Sons, New York). Examples of ingredients include, but are not limited to, an abrasive, a humectant, a surfactant, an emulsifier, a colloid, a chelating agent, an adhesive, one or more gums or resins for cohesiveness and structure, one or more flavor agents, color, a preservative, and active agents for specific effects (e.g., fluoride and whiteners). Mouthwashes can deliver active agents that cannot be provided by toothpaste because of chemical incompatibilty between the agent and the toothpaste ingredients. For example, sodium fluoride, calcium-containing abrasives, sodium lauryl sulfate, and chlorhexidine are incompatible.

The present invention is also directed to a method for degrading mutan in an oral cavity comprising applying to the oral cavity an effective amount of the compositions of the present invention. The compositions of the present invention can be applied in a dry, paste, gum, or liquid form. The composition may be a concentrate which requires dilution with a suitable quantity of water or other diluent before application. The concentrations of each component in the composition will vary depending on the use and method of application. The mutanase concentration will vary depending upon the nature of the particular composition, specifically, whether it is a concentrate or to be used directly. After application, the composition is then allowed to remain in contact with the tissues of the oral cavity for a period of time ranging from about 15 seconds to about 12 hours until removed by rinsing or brushing. Alternatively, the composition may be left indefinitely until the composition is removed by a mechanical process, e.g., drinking liquid or chewing food.

The present invention is further described by the following examples which should not be construed as limiting the scope of the invention.

EXAMPLES

Example 1

Production of Mutanase by *Penicillium purpurogenum* CBS 238.95

*Penicillium purpurogenum* CBS 238.95 was obtained from the Centraalbureau voor Schimmelcultures, Oosterstraat 1, 3742 SK Baarn, The Netherlands. The strain was cultivated at pH 6.0, 30° C., and 300 rpm in a medium comprised of 30 g of glucose, 0.5 g of yeast extract, 2 g of citric acid, 11 g of $MgSO_4$-$7H_2O$, 6 g of $K_3PO_4$-$3H_2O$, 12 g of $(NH_4)_2HPO_4$, and 6.5 g of lactic acid per liter. After 10 days of growth, the whole culture broth was centrifuged and the supernatant recovered.

Example 2

Mutanase Plate Assay

Mutanase activity was detected by the ability of a sample of the supernatant of Example 1 to produce clearing zones in mutan agar plates. The sensitivity of the plate assay was increased if the mutan was treated with dextranase.

The dextranase-treated mutan was prepared by growing *Streptococcus mutans* CBS 350.71 at pH 6.5, 37° C. (kept constant), and with an aeration rate of 75 rpm in a medium comprised of 6.5 g of NZ-Case, 6 g of yeast extract, 20 g of $(NH_4)_2SO_4$, 3 g of $K_2PO_4$, 50 g of glucose, and 0.1% Pluronic PE6100 per liter.

After 35 hours, sucrose was added to a final concentration of 60 g/liter to induce production of glucosyltransferase. The total fermentation time was 75 hours. The supernatant from the fermentation was centrifuged and filtered (sterile). Sucrose was then added to the supernatant to a final concentration of 5% (pH was adjusted to pH 7.0 with acetic acid) and the solution was stirred overnight at 37° C. The solution was filtered and the insoluble mutan was harvested on propex and washed extensively with deionized water containing 1% sodium benzoate, pH 5 (adjusted with acetic acid). Finally, the insoluble mutan was lyophilized and ground.

Ten grams of purified *Streptococcus mutans* mutan was suspended in 200 ml of 0.1M sodium acetate pH 6.0 and incubated at 30° C. for 20 hours with 50 $\mu$l of DEXTRANASE™ 50L (Novo Nordisk A/S, Bagsvaerd, Denmark). Following incubation, the suspension was centrifuged and the sediment was washed with deionized water. This step was repeated two times. The washed sediment was dried at 65° C. and ground into a powder using a coffee mill. A 1 gm quantity of the dextranase-treated mutan was suspended in 15 ml of 0.1M sodium acetate pH 6.0 and blended for 25 minutes in an Ultra Turrax homogenizer (Janke & Kunkel, IKA-Labortechnik). The blended suspension was autoclaved for 20 minutes, added to 450 ml of 2% molten agar, and poured into Petri plates. After cooling of the mutan-containing agar solution, wells were punched into the agar and enzyme samples of 10 μl were placed in the wells. The plates were incubated for 20 hours at 37° C. and mutanase activity was visualized as clear zones on a milky white background.

A 10 μl sample of the supernatant of the whole broth of *Penicillium purpurogenum* CBS 238.95 prepared as described in Example 1 produced a clearing zone on agar plates containing dextranase-treated mutan.

Example 3
High Performance Size Exclusion Chromatography Assay

The degradation of dextranase-treated mutan to soluble saccharide products by mutanase was determined by high performance size exclusion chromatography.

A 0.5% w/v suspension of dextranase-treated mutan (prepared as described in Example 2) in 0.1M sodium acetate pH 6.0 was blended in an Ultra Turrax homogenizer for 25 minutes. In an Eppendorf tube, 1 ml of the blended suspension was added to 20 μl of enzyme sample and incubated for 20 hours at 30° C. in an Eppendorf thermo-mixer followed by heat inactivation of the mutanase at 95° C. for 20 minutes. For each mutanase sample, a control was run in which the mutanase solution was first inactivated. The mutan suspensions were centrifuged and the supernatants were analyzed by injecting 25 μl onto three TSK columns—PW G4000, PW G3000, PW G2500—(Toso Haas, 7.8 mm I.D.×30 cm) connected in tandem. The saccharides were eluted with 0.4M sodium acetate pH 3.0 at a temperature of room temperature and a flow rate of 0.8 ml per minute. Eluting saccharides were detected by refractive index using a Shimadzu refractive index detector and the data collected was processed using Dionex software (AI-450, Dionex Corporation, Sunnyvale, Calif.). Dextrans and glucose were used as molecular weight standards. Mutanase activity results in the production of glucose.

A 25 μl sample of the supernatant of the whole broth of *Penicillium purpurogenum* CBS 238.95 prepared as described in Example 1 produces glucose from dextranase-treated mutan.

Example 4
Purification of *Penicillium purpurogenum* CBS 238.95 Mutanase

The *Penicillium purpurogenum* CBS 238.95 mutanase was purified from the whole broth supernatant prepared as described in Example 1 using a four-step purification method.

First, the supernatant was filtered through a 0.2 μm filter. Then 100 ml of the filtered supernatant was concentrated and equilibrated in 25 mM Tris-HCl pH 8.0 by ultrafiltration using an Amicon cell equipped with a 10,000 kDa MW-CO (molecular weight cut-off) membrane.

Second, the 50 ml concentrate was loaded at a flow rate of 1.5 ml per minute onto a XK 16/20 Fast Flow Q Sepharose (Pharmacia Biotech, Uppsala, Sweden) anion exchange column pre-equilibrated with 25 mM Tris-HCl pH 8.0. The column was then washed with two volumes of 25 mM Tris-HCl pH 8.0 before the bound proteins were eluted with a linear gradient from 0 to 1M NaCl in 25 mM Tris-HCl pH 8.0 in 3 column volumes. The fractions were assayed for mutanase activity using mutan agar plates as described in Example 2. The presence of mutanase activity was confirmed using the high performance size exclusion chromatography method described in Example 3. Fractions containing mutanase activity were pooled. Mutanase activity eluted at approximately 0.75M NaCl.

Third, the buffer in the pooled fractions was changed to 0.25M ammonium acetate pH 5.5 by equilibration by ultrafiltration using an Amicon cell equipped with a 10,000 kDa MW-CO membrane. The pooled fractions were then loaded onto a HiLoad 26/60 Superdex 75 (Pharmacia Biotech, Uppsala, Sweden) gel filtration column and the mutanase protein was eluted at 1 ml per minute with 0.25M ammonium acetate pH 5.5. The presence of mutanase activity was determined using the high performance size exclusion chromatography method described in Example 3. Fractions containing mutanase activity were pooled.

Fourth, the buffer in the pooled fractions was changed to 20 mM Tris-HCl pH 8.0 by ultrafiltration using an Amicon cell equipped with a 10,000 kDa MW-CO membrane. The pooled fractions were loaded at 1 ml per minute onto a Mono Q HR10/10 (Pharmacia Biotech, Uppsala, Sweden) column pre-equilibrated with 20 mM Tris-HCl pH 8.0. The column was then washed with two volumes of 20 mM Tris-HCl pH 8.0 before the bound proteins were eluted with a 100 ml linear gradient from 0 to 0.75M NaCl in 20 mM Tris-HCl pH 8.0. Mutanase activity was determined using the high performance size exclusion chromatography method described in Example 3. Mutanase activity eluted at approximately 0.4M NaCl.

Example 5
N-Terminal Sequencing of the *Penicillium purpurogenum* CBS 238.95 Mutanase N-terminal amino acid sequencing of the mutanase obtained from *Penicillium purpurogenum* CBS 238.95 was performed following SDS-PAGE and electroblotting using standard procedures with an Applied Biosystems 473A protein sequencer equipped with a blot cartridge and operated according to the manufacturer's instructions. The N-terminal amino acid sequence was determined to be as follows:

Xaa—Thr—Ser—Asx—Arg—Leu—Val—Phe—Ala—(His)—Phe—(Met)—Val—Gly—Ile—Val— (SEQ ID NO:1)
1                   5                        10                        15 wherein the amino acid residues at positions 10 and 12 are uncertain, but are believed to be His and Met, respectively, Xaa at position 1 designates an unidentified amino acid residue, and Asx at position 4 denotes an amino acid residue which is either Asp or Asn. This sequence is clearly distinct from the N-terminal sequence of the *Trichoderma harzianum* mutanase disclosed in Japanese Patent No. 4-58889/A shown below:

Ser—Ser—Ala—Asp—Arg—Leu—Val—Phe—Cys—His—Phe—Met—Ile—Gly—Ile—Val—     (SEQ ID NO:4)
1             5                   10                  15

Example 6
Penicillium purpurogenum CBS 238.95 DNA Extraction

Penicillium purpurogenum CBS 238.95 was grown in 25 ml of 0.5% yeast extrat-2% glucose (YEG) medium for 24 hours at 32° C. and 250 rpm. Mycelia were then collected by filtration through Miracloth (Calbiochem, La Jolla, Calif.) and washed once with 25 ml of 10 mM Tris-1 mM EDTA (TE) buffer. Excess buffer was drained from the mycelia which were subsequently frozen in liquid nitrogen. The frozen mycelia were ground to a fine powder in an electric coffee grinder, and the powder was added to 20 ml of TE buffer and 5 ml of 20% w/v sodium dodecylsulfate (SDS) in a disposable plastic centrifuge tube. The mixture was gently inverted several times to ensure mixing, and extracted twice with an equal volume of phenol:chloroform:isoamyl alcohol (25:24:1 v/v/v). Sodium acetate (3M solution) was added to give a final concentration of 0.3M and the nucleic acids were precipitated with 2.5 volumes of ice cold ethanol. The tube was centrifuged at 15,000×g for 30 minutes and the pellet was allowed to air dry for 30 minutes before resuspension in 0.5 ml of TE buffer. DNase-free ribonuclease A was added to a concentration of 100 µg/ml and the mixture was incubated at 37° C. for 30 min. Proteinase K (200 µg/ml) was then added and the mixture was incubated an additional hour at 37° C. Finally, the mixture was extracted twice with phenol:chloroform:isoamyl alcohol (25:24:1 v/v/v) before precipitating the DNA with sodium acetate and ethanol according to standard procedures. The DNA pellet was dried under vacuum, resuspended in TE buffer, and stored at 4° C.

Example 7
Hybridization Analysis of Genomic DNA

The total cellular DNA sample prepared as described in Example 6 was analyzed by Southern hybridization (Maniatis et al., 1982, Molecular Cloning, a Laboratory Manual, Cold Spring Harbor Press, Cold Spring Harbor, N.Y.). Approximately 5 µg of the DNA sample were digested with BamHI, EcoRI, or HindIII and fractionated by size on a 1% agarose gel. The gel was photographed under short wavelength UV light and soaked for 15 minutes in 0.5M NaOH-1.5M NaCl followed by 15 minutes in 1M Tris-HCl pH 8-1.5M NaCl. DNA in the gel was transferred onto a Nytran™ hybridization membrane (Schleicher & Schuell, Keene, N.H.) by capillary blotting in 20×SSPE (3M sodium chloride-0.2M sodium dibasic phosphate-0.02M disodium EDTA) according to Davis et al. (1980, Advanced Bacterial Genetics, A Manual for Genetic Engineering, Cold Spring Harbor Press, Cold Spring Harbor, N.Y.). The membrane was baked for 2 hours at 80° C. under vacuum and was soaked for 2 hours in the following hybridization buffer at 45° C. with gentle agitation: 5×SSPE, 35% formamide (v/v), 0.3% SDS, and 200 µg/ml denatured and sheared salmon testes DNA. A mutanase-specific probe fragment (approximately 1.8 kb) comprising the coding sequence of a Trichoderma harzianum mutanase cDNA (see, for example, Japanese Patent No. 4-58889/A) was radiolabeled by nick translation (Maniatis et al., supra) with α[$^{32}$P]dCTP (Amersham, Arlington Heights, Ill.) and added to the hybridization buffer at an activity of approximately 1×10$^6$ cpm per ml of buffer. The mixture was incubated with the membrane overnight at 45° C. in a shaking water bath. Following incubation, the membrane was washed once in 0.2×SSPE with 0.1% SDS at 45° C. followed by two washes in 0.2×SSPE (no SDS) at the same temperature. The membrane was dried on a paper towel for 15 minutes, then wrapped in Saran-Wrap™ and exposed to X-ray film overnight at −70° C. with intensifying screens (Kodak, Rochester, N.Y.).

Southern blotting indicated that the Trichoderma harzianum mutanase cDNA can be used as a probe under conditions of moderate stringency to identify and clone the mutanase gene from Penicillium purpurogenum CBS 238.95 shown in FIG. 1.

Example 8
DNA Libraries and Identification of Mutanase Clones

Genomic DNA libraries were constructed using the bacteriophage cloning vector λZipLox (Life Technologies, Gaithersburg, Md.) with E. coli Y1090ZL cells (Life Technologies, Gaithersburg, Md.) as a host for plating and purification of recombinant bacteriophage and E. coli DH10Bzip (Life Technologies, Gaithersburg, Md.) for excision of individual pZL1-mutanase clones. Total cellular DNA was partially digested with Tsp509I and size-fractionated on 1% agarose gels. DNA fragments migrating in the size range 3–7 kb were excised and eluted from the gel using Prep-a-Gene reagents (BioRad Laboratories, Hercules, Calif.). The eluted DNA fragments were ligated with EcoRI-cleaved and dephosphorylated λZipLox vector arms (Life Technologies, Gaithersburg, Md.), and the ligation mixtures were packaged using commercial packaging extracts (Stratagene, LaJolla, Calif.). The packaged DNA libraries were plated and amplified in Escherichia coli Y1090ZL cells (Life Technologies, Gaithersburg, Md.). The unamplified genomic library contained 4.1×10$^6$ pfu/ml (the control ligation with no genomic DNA inserts yields 2.0× 10$^4$ pfu/ml). Approximately 45,000 plaques from the library were screened by plaque-hybridization with the radiolabeled Trichoderma harzianum mutanase probe fragment described in Example 7. Eighteen positive clones which hybridize strongly to the probe were picked and ten were purified twice in E. coli Y1090ZL cells. The mutanase clones were subsequently excised from the λZipLox vector as pZL1-mutanase clones (D'Alessio et al., 1992, Focus® 14:76).

Example 9
DNA Sequence Analysis of Penicillium purpurogenum CBS 238.95 Mutanase Gene Restriction mapping of the pZL1-mutanase clones described in Example 8 was performed using standard methods (Maniatis et al., supra). DNA sequencing of the mutanase clones described in Example 8 was performed with an Applied Biosystems Model 373A Automated DNA Sequencer (Applied Biosystems, Inc., Foster City, Calif.) using a combination of shotgun DNA sequencing (Messing et al., 1981, Nucleic Acids Research 9:309–321) and the primer walking technique with dye-terminator chemistry (Giesecke et al., 1992, Journal of Virol. Methods 38: 47–60). In addition to the lac-forward and lac-reverse primers, specific oligonucleotide sequencing primers were synthesized on an Applied Biosystems Model 394 DNA/RNA Synthesizer according to the manufacturer's instructions.

Figure 2:
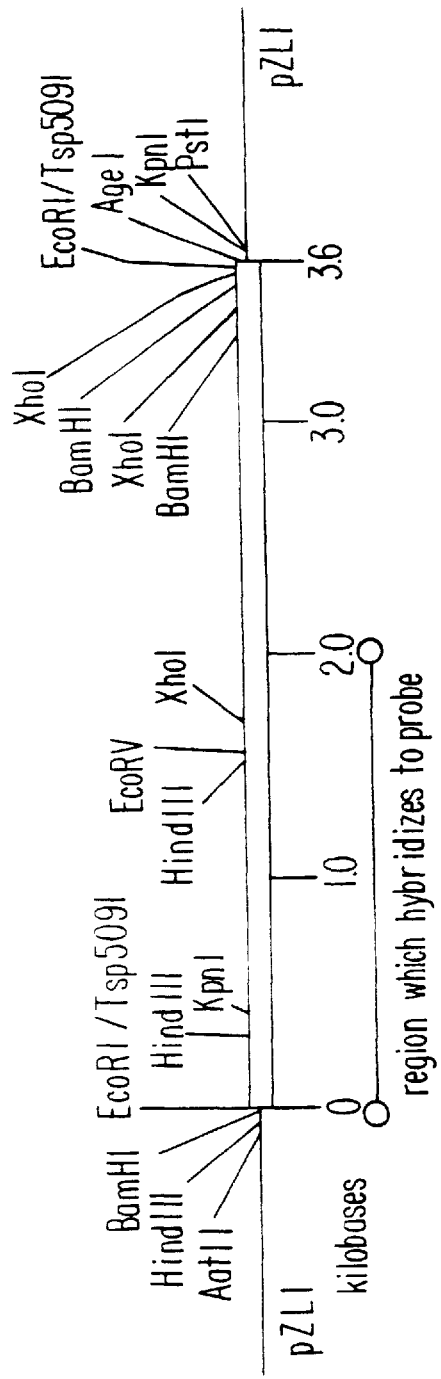
FIG. 2 shows a partial restriction map of a 3.6 kb DNA insert in clone Pp6A.

Example 10
Properties of the Penicillium purpurogenum CBS 238.95 Mutanase Gene Restriction mapping of one of the pZL1-mutanase clones designated Pp6A (E. coli INVα1F-pZL-Pp6A) reveals that the region which hybridizes under conditions of moderate stringency to the *Trichoderma harzianum* mutanase cDNA was localized near one end of a 3.6 kb genomic DNA insert shown in FIG. 2.

DNA sequencing of a portion of this segment shows an open reading frame (SEQ ID NO:2) with homology to the *Trichoderma harzianum* mutanase cDNA and the deduced amino acid sequence of the *Penicillium purpurogenum* mutanase (SEQ ID NO:3) shown in FIG. 3.

The positions of introns and exons within the *Penicillium purpurogenum* CBS 238.95 mutanase gene were assigned based on alignments of the deduced amino acid sequence to the corresponding *Trichoderma harzianum* mutanase gene product. On the basis of this comparison, the *Penicillium purpurogenum* CBS 238.95 mutanase gene was comprised of five exons (126, 532, 226, 461, and 548 bp) which are interrupted by four small introns (63, 81, 58, and 78 bp). The sizes and composition of the introns are consistent with those of other fungal genes (Gurr et al., 1987, In Kinghorn, J. R. (ed.), *Gene Structure in Eukaryotic Microbes*, pp. 93–139, IRL Press, Oxford) in that all contain consensus splice donor and is acceptor sequences as well as the consensus lariat sequence (PuCTPuAC) near the 3' end of each intervening sequence.

A comparison of the N-terminal amino acid sequence described in Example 5 with the deduced N-terminal amino acid sequence of the *Penicillium purpurogenum* CBS 238.95 mutanase gene product set forth in FIG. 3 (SEQ ID NO:3) predicted an amino terminal extension of 30 amino acids which is not present in the mature enzyme. Based on the rules of von Heijne (von Heijne, 1984, *Journal of Molecular Biology* 173: 243–251), the first 20 amino acids likely comprise a secretory signal peptide which directs the nascent polypeptide into the endoplasmic reticulum. The next 10 amino acid residues probably represent a propeptide segment which is subsequently removed by proteolytic cleavage following a dibasic Arg-Arg sequence. The mature mutanase is an acidic protein (calculated isoelectric point= 3.8) composed of 600 amino acids (MW=63,443). Since the observed molecular weight on SDS-PAGE (ca. 96,000) is considerably greater than that predicted by the deduced amino acid sequence set forth in FIG. 3 (SEQ ID NO:3), it appears likely that the mutanase contains a considerable amount of carbohydrate, possibly as much as 34% by weight. The signal peptide and propeptide portions of the *Penicillium purpurogenum* mutanase share little similarity with the *Trichoderma harzianum* mutanase shown in FIG. 4 (SEQ ID NO:5).

The deduced amino acid sequence of the mature *Penicillium purpurogenum* CBS 238.95 mutanase shares approximately 52.8% identity with the mutanase from *Trichoderma harzianum* (Japanese Patent No. 4-58889/A) shown in FIG. 4 (SEQ ID NO:5). The regions of greatest identity are located in the amino terminal half of these two proteins as well as over the last 70 residues comprising their respective C-termini. The mature *Penicillium purpurogenum* mutanase appears to be comprised of three distinct domains: (1) an amino terminal catalytic domain, (2) a Ser-Thr rich linker domain, and (3) a C-terminal polysaccharide (i.e., mutan) binding domain (residues 548–630). The Ser-Thr rich domain (residues 475–547) is composed of 62% Ser and Thr, and is bordered roughly by Cys residues at positions 477 and 547. This region may be heavily glycosylated (O-linked) in a manner similar to the Ser-Thr rich linker region of *Aspergillus niger* glucoamylase (Coutinho and Reilly, 1994, *Protein Engineering* 7:393–400).

Example 11

Expression of *Penicillium purpurogenum* CBS 238.95 mutanase in *Aspergillus oryzae*

Two synthetic oligonucleotide primers shown below were designed to amplify the *Penicillium purpurogenum* CBS 238.05 mutanase gene from plasmid pZL-Pp6A.

5'-cccatttaaatATGAAAGTCTCCAGTGCCTTC-3' (SEQ ID NO:6)

5'-cccttaattaaTTAGCTCTCTACTTGACAAGC-3' (SEQ ID NO:7)

(capital letters correspond to the sequence present in the mutanase gene)

Figure 5:
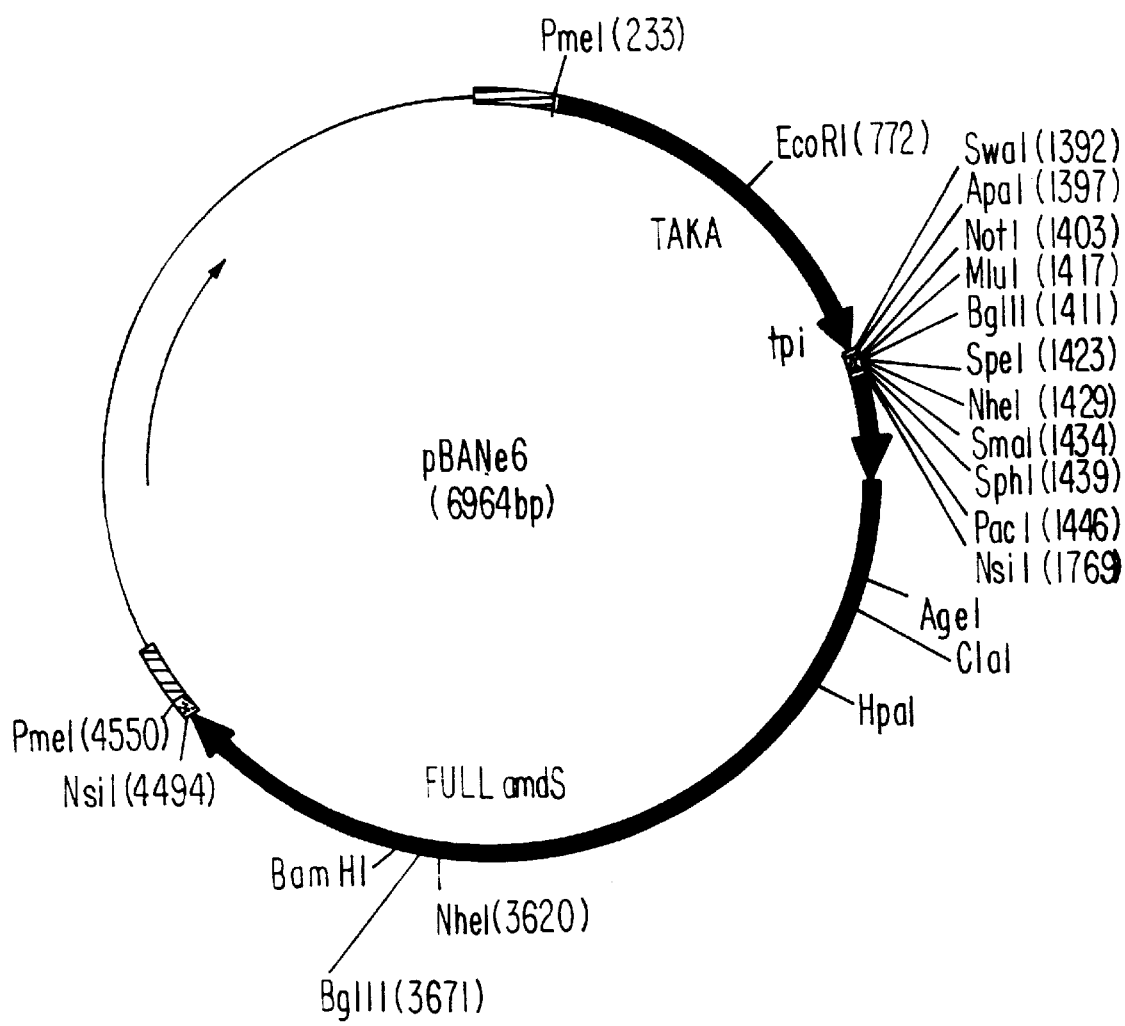
FIG. 5 shows a restriction map of pBANe6.

One hundred picomoles of each of the primers were used in a PCR reaction containing 52 ng plasmid DNA, 1× Pwo Buffer (Boehringer Mannheim, Indianapolis, Ind.), 1 mM each dATP, dTTP, dGTP, and dCTP, and 2.5 units of PwoI (Boehringer Mannheim, Indianapolis, Ind.). The amplification conditions were one cycle at 95° C. for 3 minutes, 25 cycles each at 95° C. for 1 minute, 60° C. for 1 minute, and 72° C. for 1.5 minutes, and a final cycle at 72° C. for 5 minutes. The amplified 2.2 kb DNA fragment was purified by gel electrophoresis and cut with restriction endonucleases SwaI and PacI (using conditions specified by the manufacturer). The cut fragment was cloned into plasmid pBANe6 (FIG. 5) that had been previously cut with SwaI and PacI resulting in the expression plasmid pJeRS35.

Plasmid pJeRS35 was introduced into an alkaline protease-deficient *Aspergillus oryzae* host JaL142-6 using standard protoplast transformation methods (Christensen et al. 1988, *Bio/Technology* 1419–1422). The transformation was conducted with protoplasts at a concentration of ca. 2×10$^7$ protoplasts per ml. One hundred μl of protoplasts were placed on ice with ca. 5 μg DNA for 30 minutes. One ml of SPTC (40% PEG 4000, 0.8M sorbitol, 0.05M Tris pH 8.0, 0.05M CaCl$_2$) was added and the protoplasts were incubated at room temperature for 20 minutes. Seven ml Cove agar overlay (per liter: 0.52 g of KCl, 0.52 g of MgSO$_4$-7H$_2$O, 1.52 g of KH$_2$PO$_4$, 1 ml of trace metals described below, 0.8M sucrose, and 1% low melt agar) were added to the transformation prior to plating onto COVE transformation plates (per liter: 0.52 g of KCl, 0.52 g of MgSO$_4$-7H$_2$O, 1.52 g of KH$_2$PO$_4$, 1 ml of trace metals described below, 342.3 g of sucrose, 25 g of Noble agar, 10 ml of 1M acetamide, 10 ml of 3M CsCl). The trace metals solution (1000×) is comprised of 22 g of ZnSO$_4$-7H$_2$O, 11 g of H$_3$BO$_3$, 5 g of MnCl$_2$-4H$_2$O, 5 g of FeSO$_4$-7H$_2$O, 1.6 g of CoCl$_2$-5H$_2$O, 1.6 g of (NH$_4$)$_6$Mo$_7$O$_{24}$, and 50 g of Na$_4$EDTA per liter. Plates were incubated 5–7 days at 34° C. Transformants were transferred to plates of the same medium and incubated 3–5 days at 37° C. The transformants were purified by streaking spores and picking isolated colonies using the same plates under the same conditions. Totally, 40 transformants were recovered by their ability to grow on COVE medium using acetamide as sole nitrogen source.

The transformants were grown for 3 days at 34° C. with agitation in shake flasks containing 20 ml of MY50N medium comprised of 62 g of Nutriose, 2.0 g of MgSO$_4$-7H$_2$O, 2.0 g of KH$_2$PO$_4$, 4.0 g of citric acid, 8.0 g of yeast extract, 2.0 g of urea, 0.1 g of CaCl$_2$, and 0.5 ml of trace metals solution per liter adjusted to pH 6.0. The trace metals solution consisted of 2.2 g of ZnSO$_{4x}$7H$_2$O, 1.1 g of H$_3$BO$_3$, 0.5 g of MnCl$_2$-4H$_2$O, 0.5 g of FeSO$_4$×7H$_2$O, 0.16 g of CoCl$_2$×5H$_2$O, 0.16 g of (NH$_4$)$_6$Mo$_7$O$_{24}$, and 5 g of Na$_4$EDTA per 100 ml of deionized water.

Mutan assay plates were prepared by blending a suspension of 1% (v/w) mutan, 1% agarose in 0.1M sodium acetate pH 5.5 buffer for 20 minutes at 4° C. The agarose was melted by heating and 150 mm petri plates were poured. After solidification, small wells (ca. 40 μl equivalent volume) were punched in the plates. Thirty-five μl volumes of centrifuged broth of the 40 grown transformant cultures (and one untransformed control) were pipetted into the wells and the plates were incubated at 37° C. After overnight incubation, 14 of the transformant wells showed opaque clearing zones (the control showed no clearing zone).

The broths from the positive transformants were analyzed by SDS-PAGE using 8–16% polyacrylamide Novex gels (Novex, San Diego, Calif.) according to the manufacturer's instructions. The transformants showed a prominent band at ca. 96 kDa while no band of this size was observed from the broth of the control culture. The 96 kDa band from one of the transformant cultures was re-isolated by SDS-PAGE and blot transferred to PVDF membrane (Novex, San Diego, Calif.) using 10 mM CAPS (3-[cyclohexylamino]-1-propanesulfonic acid) in 10% Methanol, pH=11.0 for 2 hours. The PVDF membrane was stained with 0.1% Coomassie® Blue R-250 in 40% MeOH/1% acetic acid for 20 seconds. The stained band was excised and subjected to N-terminal sequencing on a Applied Biosystems Inc. Model 476A protein sequencer (Applied Biosystems, Foster City, Calif.) using a blot cartridge and liquid phase trifluoroacetic acid delivery according to manufacturer's instructions. The results showed the expected N-terminus of the mutanase based on the DNA sequence. N-terminal processing followed a Kex-2 cleavage site. The N-terminal sequence was determined to be STSDRLVFAHFMVGIVSDRTSA (SEQ ID NO:1).

Example 12

Purification and characterization of recombinant *Penicillium purpurogenum* mutanase One of the transformants described in Example 11, *Aspergillus oryzae* JeRS323, was grown at 30° C., 200 rpm for 4 days in 1.0 liter shake flasks containing 250 ml of a medium consisting of of 10 g of yeast extract and 20 g of peptone per liter supplemented with 2% maltose. The whole culture broths were filtered through Miracloth.

Mutan, prepared as described in Example 2, was washed with 0.1M sodium acetate pH 5.5 buffer and then suspended in an amount of 15.6 g to 780 ml of 0.45 μm filtered shake flask broth to provide a 2% solution. The suspension was adjusted to pH 5.5 and then mixed at 4° C. for 1 hour. The suspension was then filtered on a sintered glass filter funnel, washed 4 times with 0.1M sodium acetate pH 5.5 buffer (total volume: 1110 ml), and finally 6 times with deionized water (total volume: 1250 ml). After each washing step, the suspension was filtered and the filtrate fractions collected. Elution of the mutanase was determined by measuring production of soluble reducing sugars released from mutan. Specifically, 0.1 ml of 5% mutan in 50 mM sodium acetate pH 5.5 buffer (allowed to swell at least for 1 hour) was added to 0.3 ml of each fraction (diluted in deionized water) in round bottomed Eppendorf vials (to ensure sufficient agitation) and incubated for 15 minutes at 40° C. with vigorous shaking. The reaction was terminated by adding 0.1 ml of 0.4M NaOH. The samples were centrifuged, filtered through 0.45 μm filters (Millipore, Bedford, Mass.), and the filtrates collected. A volume of 100 μl of each filtrate were added to 750 μl of ferricyanide reagent (0.4 g/l $K_3Fe(CN)_6$, 20 g/l $Na_2CO_3$) in Eppendorf vials and incubated 15 minutes at 85° C. After allowing the samples to cool, the decrease in absorption at 420 nm was measured. A dilution series of glucose was included as a standard. Substrate and enzyme blanks were included as controls. Samples were run in duplicates. One mutanase unit (MU) is defined as the amount of enzyme which produces 1 μmole of reducing sugars (measured as glucose equivalents) per minute from mutan at pH 5.5 and 40° C.

The recombinant mutanase eluted during the washing with water. The filtrates were pooled, 0.7 μm filtered (Whatman, Fairfield, N.J.), concentrated on a Microsep™ Microconcentrator (Filtron, Northborough, Mass.) equipped with a 10 kDa MW-CO membrane, and further concentrated to 25 ml on an Amicon cell equipped with a YM10 membrane (Amicon, Beverly, Mass.). The purification resulted in a 129 fold purification with a yield of around 20% (Table 1). The relative low yield can be explained by an incomplete adsorption on the mutan and some leakage of mutanase during the washing steps. The purity of the mutanase was estimated to be >95% by SDS-PAGE and IEF with a molecular weight around 90 kDa and an isoelectric point (pI) of approximately pH 3 (theoretical pI=3.95). The N-terminal amino acid sequence was verified to be Ser-Thr-Ser-Asp-Arg- (SEQ ID NO:1).

TABLE 1

Purification of recombinant *Penicillium purpurogenum* mutanase

| Sample | Volume (ml) | $A_{280}$ | $A_{260}$ | Activity (MU/ml) | Total Activity (MU) | Yield Yield (%) |
|---|---|---|---|---|---|---|
| Broth | 780 | 19.8 | 27.3 | 2.2 | 1716 | 100 |
| Purified | 25 | 0.90 | 0.65 | 12.8 | 320 | 19 |

Temperature profiles were obtained by incubating the assay mixture (50 mM sodium acetate pH 5.5 or 50 mM sodium phosphate pH 7 buffer) using the procedure above at various temperatures. pH profiles were obtained by suspending the mutan in 50 mM buffer at various pH (glycine-HCl for pH 3–3.5, sodium acetate for pH 4–5.5, and sodium phosphate for pH 6–7.5).

Figure 6:
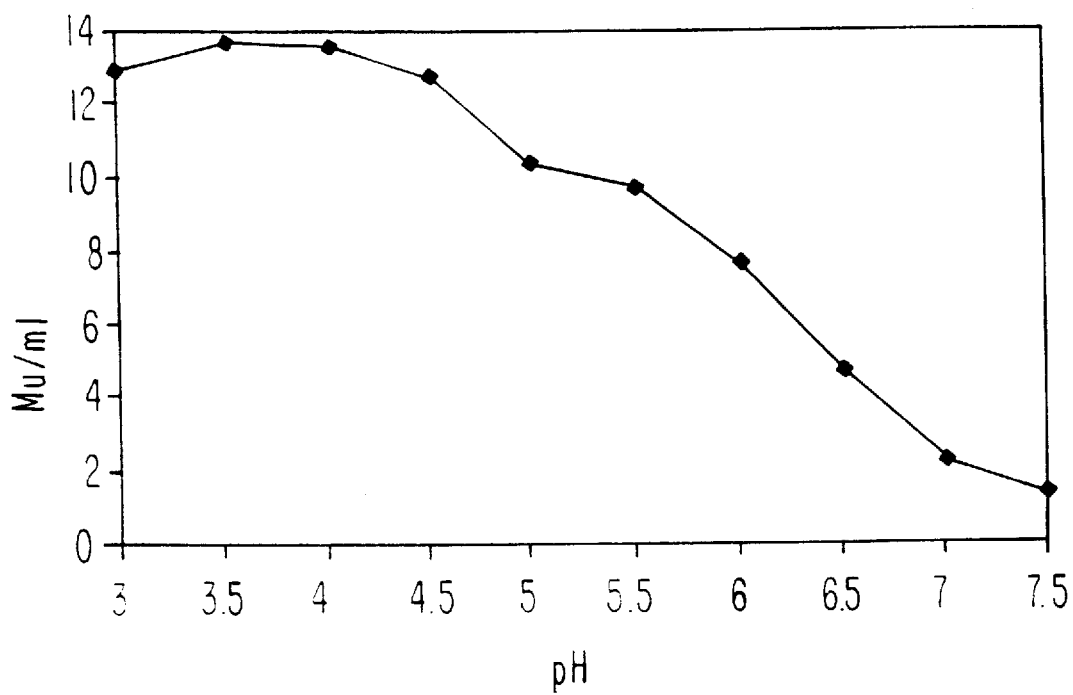
FIG. 6 shows the pH profile of the *Penicillium purpurogenum* CBS 238.95 mutanase.
Figure 7:
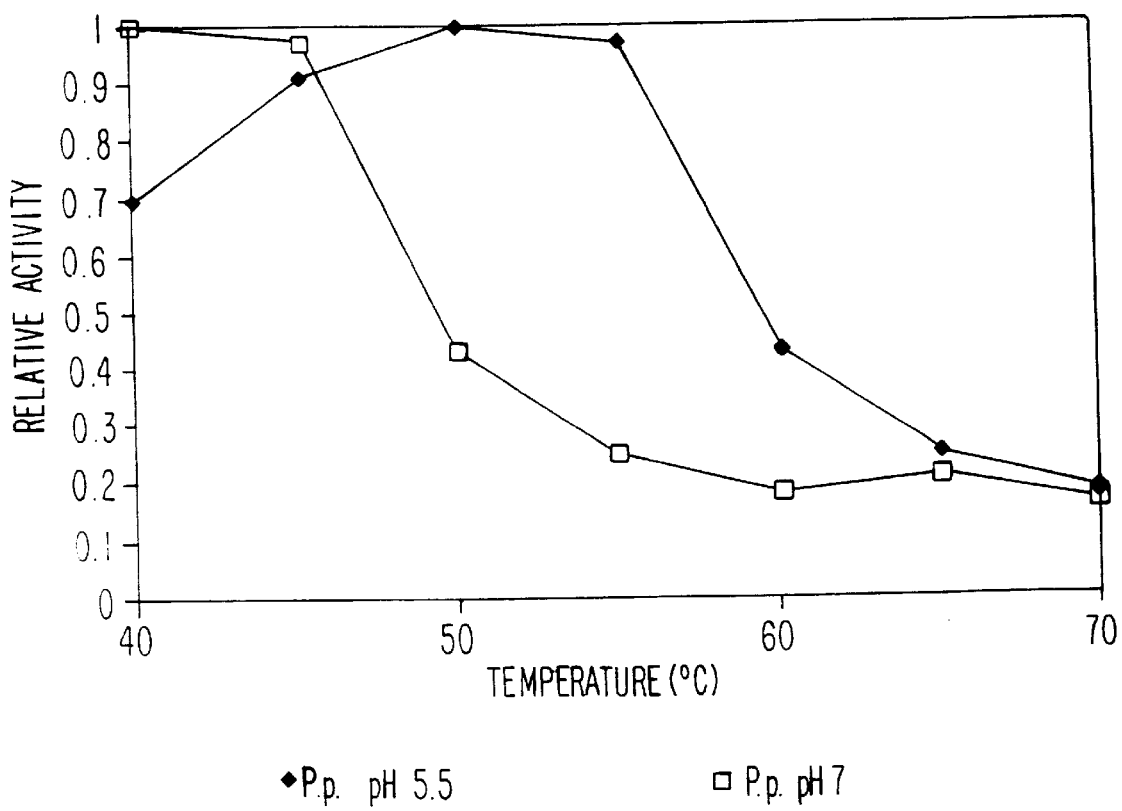
FIG. 7 shows the temperature profile of the *Penicillium purpurogenum* CBS 238.95 mutanase.

The pH- and temperature-profiles for the purified recombinant *Penicillium purpurogenum* mutanase are shown in FIGS. 6 and 7, respectively. The enzyme exhibits a fairly broad pH optimum around pH 3.5–5 and temperature optimum around 40°–45° C. at pH 7 and 50°–55° C. at pH 5.5.

Binding isotherms were obtained by incubating various concentrations of the purified recombinant *Penicillium purpurogenum* mutanase in a 0.2% suspension of mutan in 0.1M sodium phosphate pH 7 buffer for 1 hour at 4° C. with stirring. Samples were then centrifuged for 10 minutes at 15000×g and the amount of enzyme left in the supernatant determined by fluorescence spectrometry using a Perkin Elmer LS50 fluorescence spectrometer with excitation at 280 nm and emission at 345 nm. A fluorescence standard curve was constructed based on the purified mutanase.

The binding isotherm observed for the purified recombinant *Penicillium purpurogenum* mutanase binding to mutan could be fitted using the simple Langmuir model for adsorption on solid surfaces. The *Penicillium purpurogenum* mutanase show similar strong affinity for the mutan with a desorption constant ($K_d$) around 0.111±0.016 μM and a maximum binding capacity ($A_{max}$) of 0.244±0.012 μmol enzyme/g mutan.

Differential scanning calorimetry of the purified recombinant *Penicillium purpurogenum* mutanase was performed using a MicroCal MC-2 instrument according to the is manufacturer's instructions. The scan was performed from 5° C. to 95° C. at a constant scan rate of 90C per hour. A midpoint denaturation temperature of around 46° C. at pH 7 was observed for the *Penicillium purpurogenum* mutanase.

Deposit of Biological Materials

The following strain has been deposited according to the Budapest Treaty in the Agricultural Research Service Patent Culture Collection (NRRL), Northern Regional Research Laboratory, 1815 University Street, Peoria, Ill. 61604, U.S.A.

| Strain | Accession Number | Deposit Date |
|---|---|---|
| *E. coli* INVα1F (pZL-Pp6A) | NRRL B-21518 | January 18, 1996 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of each deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. An isolated nucleic acid sequence comprising a nucleic acid sequence which encodes a polypeptide having mutanase activity, selected from the group consisting of:
   (a) a polypeptide with an amino acid sequence of SEQ ID NO:3;
   (b) a polypeptide which is encoded by a nucleic acid sequence which hybridizes under high stringency conditions with (i) the nucleic acid sequence of SEQ ID NO:2, or (ii) its complementary strand;
   (c) a nucleic acid sequence having the sequence of SEQ ID NO:2;
   (d) a polypeptide with an amino acid sequence which has at least 60% identity with the amino acid sequence of SEQ ID NO:3; and
   (e) a 'mutanase encoding' fragment of (a), (b), (c), or (d).

2. The nucleic acid sequence according to claim 1, wherein the nucleic acid sequence encodes a polypeptide obtained from a Penicillium strain.

3. The nucleic acid sequence according to claim 2, wherein the nucleic acid sequence encodes a polypeptide obtained from *Penicillium purpurogenum* or a synonym or teleomorph thereof.

4. The nucleic acid sequence according to claim 3, wherein the nucleic acid sequence encodes a polypeptide obtained from *Penicillium purpurogenum* CBS 238.95 or a mutant strain thereof.

5. The nucleic acid sequence according to claim 1, which encodes a polypeptide which has an amino acid sequence which has at least 60% identity with the amino acid sequence of SEQ ID NO:3.

6. The nucleic acid sequence according to claim 1, which hybridizes under high stringency conditions with (a) the nucleic acid sequence of SEQ ID NO:2 or (b) its complementary strand or 'a mutanase encoding' fragment thereof.

7. The nucleic acid sequence according to claim 1, wherein the nucleic acid sequence is contained in plasmid pZL-Pp6A which is contained in *Escherichia coli* NRRL B-21518.

8. The nucleic acid sequence according to claim 1, wherein the nucleic acid sequence is set forth in SEQ ID NO:2.

9. A nucleic acid construct comprising the nucleic acid sequence of claim 1 operably linked to one or more control sequences which direct the expression of the polypeptide in a suitable expression host.

10. A recombinant expression vector comprising the nucleic acid construct of claim 9, a promoter, and transcriptional and translational stop signals.

11. The vector according to claim 10, further comprising a selectable marker.

12. A recombinant host cell comprising the nucleic acid construct of claim 9.

13. The cell according to claim 12, wherein the host cell is a bacterial or fungal cell.

14. The cell according to claim 13, wherein the bacterial cell is a Bacillus, Pseudomonas, or Streptomyces cell.

15. The cell according to claim 13, wherein the fungal cell is a filamentous fungal or yeast cell.

16. The cell according to claim 15, wherein the filamentous fungal cell is a cell of a species of Acremonium, Aspergillus, Fusarium, Humicola, Mucor, Myceliophthora, Neurospora, Penicillium, Thielavia, Tolypocladium, or Trichoderma.

17. The cell according to claim 15, wherein the yeast cell is a cell of a species of Candida, Kluyveromyces, Pichia, Saccharomyces, Schizosaccharomyces or Yarrowia.

18. A method for producing the polypeptide of claim 1 comprising (a) cultivating a host cell comprising a nucleic acid construct comprising a nucleic acid sequence encoding the polypeptide under conditions conducive to expression of the polypeptide; and (b) recovering the polypeptide.

19. The nucleic acid sequence of claim 5 which encodes a polypeptide having an amino acid sequence with at least 70% identity with the amino acid sequence of SEQ ID NO:3.

20. The nucleic acid sequence of claim 19 which encodes a polypeptide having an amino acid sequence with at least 80% identity with the amino acid sequence of SEQ ID NO:3.

21. The nucleic acid sequence of claim 20 which encodes a polypeptide having an amino acid sequence with at least 90% identity with the amino acid sequence of SEQ ID NO:3.

22. The nucleic acid sequence of claim 21 which encodes a polypeptide having an amino acid sequence with at least 95% identity with the amino acid sequence of SEQ ID NO:3.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
( A ) LENGTH: 22 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

```
Ser  Thr  Ser  Asp  Arg  Leu  Val  Phe  Ala  His  Phe  Met  Val  Gly  Ile  Val
1              5                        10                           15

Ser  Asp  Arg  Thr  Ser  Ala
             20
```

( 2 ) INFORMATION FOR SEQ ID NO:2:

( i ) SEQUENCE CHARACTERISTICS:
( A ) LENGTH: 2523 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: join(41..166, 230..760, 842..1069, 1128..1586, 1665..2210)

( i x ) FEATURE:
( A ) NAME/KEY: sig_peptide
( B ) LOCATION: 41..130

( i x ) FEATURE:
( A ) NAME/KEY: mat__eptide
( B ) LOCATION: join(131..166, 230..760, 842..1069, 1128..1586, 1665..2210)

( x i ) SEQUENCE DESCRIPTION: SEQ ID NO:2:

AATTGTGCCC  TAAACCTCCT  CCTGGAGGAA  CACACTCAAG  ATG AAA GTC TCC AGT    55

|     |     |     |     |     |     | Met | Lys | Val | Ser | Ser |     |     |     |     |     |      |
|-----|-----|-----|-----|-----|-----|-----|-----|-----|-----|-----|-----|-----|-----|-----|-----|------|
|     |     |     |     |     |     |     | -30 |     |     |     |     |     |     |     |     |      |

```
GCC  TTC  GCG  GCG  ACG  CTG  TCC  GCA  ATT  ATA  GCT  GCG  TGC  TCA  GCT  CTT       103
Ala  Phe  Ala  Ala  Thr  Leu  Ser  Ala  Ile  Ile  Ala  Ala  Cys  Ser  Ala  Leu
-25            -20                 -15                      -10

CCT  TCT  GAC  TCA  ATG  GTT  TCG  AGG  CGA  AGC  ACA  TCG  GAC  CGT  CTC  GTG       151
Pro  Ser  Asp  Ser  Met  Val  Ser  Arg  Arg  Ser  Thr  Ser  Asp  Arg  Leu  Val
               -5                        1                       5

TTC  GCG  CAT  TTC  ATG  GTAAACATCC  ATCTCGAATA  TGAGGCACAT  AGTCAGTGAC             206
Phe  Ala  His  Phe  Met
               10

GATAGATTGG  CTGACTTCAT  CAG  GTT  GGT  ATC  GTC  AGT  GAC  CGG  ACC  AGT             256
                        Val  Gly  Ile  Val  Ser  Asp  Arg  Thr  Ser
                             15                           20

GCT  AGC  GAT  TAT  GAC  GCC  GAC  ATG  CAG  GGT  GCT  AAA  GCT  TAT  GGA  ATT       304
Ala  Ser  Asp  Tyr  Asp  Ala  Asp  Met  Gln  Gly  Ala  Lys  Ala  Tyr  Gly  Ile
               25                 30                      35

GAC  GCC  TTT  GCA  TTG  AAT  ATC  GGT  ACC  GAT  ACC  TTC  AGC  GAC  CAG  CAA       352
Asp  Ala  Phe  Ala  Leu  Asn  Ile  Gly  Thr  Asp  Thr  Phe  Ser  Asp  Gln  Gln
               40                 45                      50

CTG  GGG  TAT  GCC  TAC  GAG  TCT  GCG  GCA  AAC  AAT  GAC  ATG  AAA  GTG  TTC       400
Leu  Gly  Tyr  Ala  Tyr  Glu  Ser  Ala  Ala  Asn  Asn  Asp  Met  Lys  Val  Phe
     55                      60                      65

ATT  TCA  TTC  GAT  TTC  AAC  TGG  TGG  TCC  ACC  AGC  CAG  GCC  ACC  GAA  ATT       448
Ile  Ser  Phe  Asp  Phe  Asn  Trp  Trp  Ser  Thr  Ser  Gln  Ala  Thr  Glu  Ile
70                       75                      80                       85

GGC  CAA  AAG  ATT  GCC  CAG  TAC  GGT  AGC  CTA  CCA  GGC  CAG  CTC  ATG  TAT       496
Gly  Gln  Lys  Ile  Ala  Gln  Tyr  Gly  Ser  Leu  Pro  Gly  Gln  Leu  Met  Tyr
               90                      95                      100

GAT  GAC  AAG  ATT  TTC  GTC  TCG  TCG  TTT  GCT  GGC  GAC  GGT  GTA  GAC  GTG       544
Asp  Asp  Lys  Ile  Phe  Val  Ser  Ser  Phe  Ala  Gly  Asp  Gly  Val  Asp  Val
               105                     110                     115

GCA  GCA  TTG  AAG  TCA  GCT  GCT  GGC  GGC  AAT  GTG  TTC  TTC  GCT  CCA  AAC       592
Ala  Ala  Leu  Lys  Ser  Ala  Ala  Gly  Gly  Asn  Val  Phe  Phe  Ala  Pro  Asn
               120                     125                     130

TTC  CAT  CCA  TCG  TAT  GGT  ACA  GAC  CTG  TCG  GAT  GTC  GAT  GGT  CTT  CTC       640
Phe  His  Pro  Ser  Tyr  Gly  Thr  Asp  Leu  Ser  Asp  Val  Asp  Gly  Leu  Leu
     135                     140                     145

AAC  TGG  ATG  GGC  TGG  CCT  AGC  AAT  GGT  AAT  AAC  AAG  GCT  CCA  ACT  GCC       688
Asn  Trp  Met  Gly  Trp  Pro  Ser  Asn  Gly  Asn  Asn  Lys  Ala  Pro  Thr  Ala
150                      155                     160                      165

GGT  GCC  AAC  GTT  ACC  GTT  GAG  GAA  GGG  GAC  GAG  GAA  TAT  ATA  ACT  GCT       736
Gly  Ala  Asn  Val  Thr  Val  Glu  Glu  Gly  Asp  Glu  Glu  Tyr  Ile  Thr  Ala
               170                     175                     180

TTG  GAT  GGC  AAG  CCC  TAC  ATT  GCT  GTCAGTCGCC  TAACCCTACC  TCCTAGCCTT           790
Leu  Asp  Gly  Lys  Pro  Tyr  Ile  Ala
               185

GGAGCAAAAC  GATTCAGTTT  GGCTGACCTT  TTCTTTTTTC  TTCTTCACTA  G  CCG  GCC             847
                                                                Pro  Ala
                                                                190

TCA  CCA  TGG  TTC  TCT  ACG  CAT  TTT  GGG  CCA  GAG  GTG  ACA  TAC  AGC  AAG       895
Ser  Pro  Trp  Phe  Ser  Thr  His  Phe  Gly  Pro  Glu  Val  Thr  Tyr  Ser  Lys
               195                     200                     205

AAC  TGG  GTT  TTC  CCA  TCT  GAT  TTG  CTT  TTC  TAC  CAG  CGT  TGG  AAT  GAT       943
Asn  Trp  Val  Phe  Pro  Ser  Asp  Leu  Leu  Phe  Tyr  Gln  Arg  Trp  Asn  Asp
          210                     215                     220

CTA  TTG  AAT  TTG  GGC  CCT  CAA  TTC  ATT  GAA  GTG  GTC  ACC  TGG  AAT  GAC       991
Leu  Leu  Asn  Leu  Gly  Pro  Gln  Phe  Ile  Glu  Val  Val  Thr  Trp  Asn  Asp
225                      230                     235

TAT  GGT  GAA  TCG  CAA  TAT  GTC  GGA  CCT  CTG  AAC  TCT  CCT  CAT  ACA  GAC      1039
```

```
Tyr Gly Glu Ser Gln Tyr Val Gly Pro Leu Asn Ser Pro His Thr Asp
240                 245                 250                 255

GAT GGC TCC TCT CGA TGG GCG AAT GAC ATG GTAAGCCATC TTGTGTAGGT           1089
Asp Gly Ser Ser Arg Trp Ala Asn Asp Met
                260                 265

ATCGGTGTTT TGTTTCTATG CTAACATCAA GAAACTAG CCT CAC GAT GGC TGG           1142
                                          Pro His Asp Gly Trp
                                                          270

CTG GAT CTG GCA AAG CCC TAC ATC GCG GCA TTC CAC GAC GGG GCC ACT         1190
Leu Asp Leu Ala Lys Pro Tyr Ile Ala Ala Phe His Asp Gly Ala Thr
                275                 280                 285

TCG CTA TCA TCA TCC TAC ATC ACC GAA GAC CAG CTC ATC TAC TGG TAT         1238
Ser Leu Ser Ser Ser Tyr Ile Thr Glu Asp Gln Leu Ile Tyr Trp Tyr
                290                 295                 300

CGG CCT CAA CCA CGA CTC ATG GAC TGC GAC GCA ACT GAT ACC TGC ATG         1286
Arg Pro Gln Pro Arg Leu Met Asp Cys Asp Ala Thr Asp Thr Cys Met
                305                 310                 315

GTT GCT GCC AAC AAT GAC ACG GGC AAC TAT TTC GAG GGC AGA CCC AAT         1334
Val Ala Ala Asn Asn Asp Thr Gly Asn Tyr Phe Glu Gly Arg Pro Asn
                320                 325                 330

GGG TGG GAA AGC ATG GAG GAC GCT GTC TTC GTG GTT GCT TTG CTC CAG         1382
Gly Trp Glu Ser Met Glu Asp Ala Val Phe Val Val Ala Leu Leu Gln
335                 340                 345                 350

TCT GCT GGA ACG GTT CAG GTC ACT TCA GGC CCT AAT ACC GAG ACA TTT         1430
Ser Ala Gly Thr Val Gln Val Thr Ser Gly Pro Asn Thr Glu Thr Phe
                355                 360                 365

GAT GCT CCT GCT GGT GCA AGC GCC TTC CAG GTT CCC ATG GGC TTC GGC         1478
Asp Ala Pro Ala Gly Ala Ser Ala Phe Gln Val Pro Met Gly Phe Gly
                370                 375                 380

CCC CAG AGC TTC TCC CTG TCG CGG GAT GGC GAG ACA GTA TTG TCT GGA         1526
Pro Gln Ser Phe Ser Leu Ser Arg Asp Gly Glu Thr Val Leu Ser Gly
                385                 390                 395

ACA AGC TTG AAG GAT ATC ATT GAT GGA TGC TTG TGC GGA ATC TAC AAC         1574
Thr Ser Leu Lys Asp Ile Ile Asp Gly Cys Leu Cys Gly Ile Tyr Asn
                400                 405                 410

TTC AAC GCC TAT GTAAGAACTG CCGTGTCTTT TGTATATCTG AATATGTTTC             1626
Phe Asn Ala Tyr
415

CAAGGTTATT GACATGGGAA AAAAAAAAAA AAATTCAG GTG GGC TCT CTG CCA           1679
                                          Val Gly Ser Leu Pro
                                                          420

GCA ACT TTC TCC GAT CCA CTC GAG CCA CCT TCT CTC AAC GCC TTC AGC         1727
Ala Thr Phe Ser Asp Pro Leu Glu Pro Pro Ser Leu Asn Ala Phe Ser
425                 430                 435

GAA GGC TTG AAG GTT TCG ACA TGC AGC GCG ACA CCA TCT TTG GGA TTG         1775
Glu Gly Leu Lys Val Ser Thr Cys Ser Ala Thr Pro Ser Leu Gly Leu
440                 445                 450                 455

ACA TCG ACC ACT CCA CCA GAG ACC ATT CCT ACA GGC ACG ATT ACT CCA         1823
Thr Ser Thr Thr Pro Pro Glu Thr Ile Pro Thr Gly Thr Ile Thr Pro
                460                 465                 470

GGA TCA GCT ATT ACA GGT GCT GCA ACA ACT ACC TCT ACC ATC TCG ACC         1871
Gly Ser Ala Ile Thr Gly Ala Ala Thr Thr Thr Ser Thr Ile Ser Thr
                475                 480                 485

ACC TCC ACG ATT TCC ACG ACC TCA ACT TTT ATC TCA ACT ACC ACC ACC         1919
Thr Ser Thr Ile Ser Thr Thr Ser Thr Phe Ile Ser Thr Thr Thr Thr
                490                 495                 500

ACC ACG TCC AGT GCT GCT ACC TCC ACC ACC ACC GGA ACT TGC ATC GCC         1967
Thr Thr Ser Ser Ala Ala Thr Ser Thr Thr Thr Gly Thr Cys Ile Ala
                505                 510                 515

GGC ACT GGC CCT GAC AAC TAT TCT GGC CTG TGT TCC TTC TGC TGT AAC         2015
```

-continued

```
Gly  Thr  Gly  Pro  Asp  Asn  Tyr  Ser  Gly  Leu  Cys  Ser  Phe  Cys  Cys  Asn
520                 525                      530                      535

TAC  GGC  TAC  TGT  CCG  GGC  TCC  GAT  GGT  TCG  GCC  GGC  CCG  TGT  ACA  TGC        2063
Tyr  Gly  Tyr  Cys  Pro  Gly  Ser  Asp  Gly  Ser  Ala  Gly  Pro  Cys  Thr  Cys
                    540                      545                      550

ACG  GCC  TAT  GGA  GAT  CCA  GTT  CCT  ACG  CCT  CCA  GTA  ACA  GGA  ACA  GTT        2111
Thr  Ala  Tyr  Gly  Asp  Pro  Val  Pro  Thr  Pro  Pro  Val  Thr  Gly  Thr  Val
                    555                      560                      565

GGC  GTT  CCG  CTT  GAT  GGC  GAG  GGT  GAC  AGT  TAC  TTG  GGT  CTG  TGT  AGT        2159
Gly  Val  Pro  Leu  Asp  Gly  Glu  Gly  Asp  Ser  Tyr  Leu  Gly  Leu  Cys  Ser
          570                      575                      580

TTT  GCC  TGC  AAC  CAC  GGC  TAT  TGC  CCG  TCT  ACT  GCT  TGT  CAA  GTA  GAG        2207
Phe  Ala  Cys  Asn  His  Gly  Tyr  Cys  Pro  Ser  Thr  Ala  Cys  Gln  Val  Glu
          585                      590                      595

AGC  TGAGAGGTGC  CACTATCTAG  GTAATACCAT  GTTAAAGTAA  TACCTAGGTA                        2260
Ser
600

CTCTGTGTCT  AGCTTGAGAG  ATGGCAGGGT  ATCTAGTTCT  ATCTTAAATA  TAAGATTTCT                2320

CCAACTTACA  TGATTTTGAT  GCACATGGAT  AGGTAGACCT  GGACAGTGAA  GGGCAATACT                2380

TAAATAATGC  AAACAGACAC  TGGATCTATA  TCGTTCAACT  CAGTTGGCCA  AAGACTAGTC                2440

GTGAAAAAAA  CACCCTTTCG  AACAAAAACC  TTCTTCGCTG  CATCAACGCA  GTCCAAAATA                2500

AGTCCAATCC  CCTCCACCAT  GAA                                                           2523
```

( 2 ) INFORMATION FOR SEQ ID NO:3:

( i ) SEQUENCE CHARACTERISTICS:
        ( A ) LENGTH: 630 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Met  Lys  Val  Ser  Ser  Ala  Phe  Ala  Ala  Thr  Leu  Ser  Ala  Ile  Ile  Ala
-30                 -25                      -20                      -15

Ala  Cys  Ser  Ala  Leu  Pro  Ser  Asp  Ser  Met  Val  Ser  Arg  Arg  Ser  Thr
               -10                      -5                            1

Ser  Asp  Arg  Leu  Val  Phe  Ala  His  Phe  Met  Val  Gly  Ile  Val  Ser  Asp
          5                        10                       15

Arg  Thr  Ser  Ala  Ser  Asp  Tyr  Asp  Ala  Asp  Met  Gln  Gly  Ala  Lys  Ala
     20                       25                       30

Tyr  Gly  Ile  Asp  Ala  Phe  Ala  Leu  Asn  Ile  Gly  Thr  Asp  Thr  Phe  Ser
35                       40                       45                       50

Asp  Gln  Gln  Leu  Gly  Tyr  Ala  Tyr  Glu  Ser  Ala  Ala  Asn  Asn  Asp  Met
               55                       60                       65

Lys  Val  Phe  Ile  Ser  Phe  Asp  Phe  Asn  Trp  Trp  Ser  Thr  Ser  Gln  Ala
               70                       75                       80

Thr  Glu  Ile  Gly  Gln  Lys  Ile  Ala  Gln  Tyr  Gly  Ser  Leu  Pro  Gly  Gln
          85                       90                       95

Leu  Met  Tyr  Asp  Asp  Lys  Ile  Phe  Val  Ser  Ser  Phe  Ala  Gly  Asp  Gly
     100                      105                      110

Val  Asp  Val  Ala  Ala  Leu  Lys  Ser  Ala  Ala  Gly  Gly  Asn  Val  Phe  Phe
115                      120                      125                      130

Ala  Pro  Asn  Phe  His  Pro  Ser  Tyr  Gly  Thr  Asp  Leu  Ser  Asp  Val  Asp
               135                      140                      145

Gly  Leu  Leu  Asn  Trp  Met  Gly  Trp  Pro  Ser  Asn  Gly  Asn  Asn  Lys  Ala
               150                      155                      160
```

```
Pro Thr Ala Gly Ala Asn Val Thr Val Glu Glu Gly Asp Glu Glu Tyr
        165                 170                 175

Ile Thr Ala Leu Asp Gly Lys Pro Tyr Ile Ala Pro Ala Ser Pro Trp
        180                 185                 190

Phe Ser Thr His Phe Gly Pro Glu Val Thr Tyr Ser Lys Asn Trp Val
195             200                 205                     210

Phe Pro Ser Asp Leu Leu Phe Tyr Gln Arg Trp Asn Asp Leu Leu Asn
                215                 220                 225

Leu Gly Pro Gln Phe Ile Glu Val Val Thr Trp Asn Asp Tyr Gly Glu
            230                 235                 240

Ser Gln Tyr Val Gly Pro Leu Asn Ser Pro His Thr Asp Asp Gly Ser
        245                 250                 255

Ser Arg Trp Ala Asn Asp Met Pro His Asp Gly Trp Leu Asp Leu Ala
    260                 265                 270

Lys Pro Tyr Ile Ala Ala Phe His Asp Gly Ala Thr Ser Leu Ser Ser
275                 280                 285                 290

Ser Tyr Ile Thr Glu Asp Gln Leu Ile Tyr Trp Tyr Arg Pro Gln Pro
                295                 300                 305

Arg Leu Met Asp Cys Asp Ala Thr Asp Thr Cys Met Val Ala Ala Asn
            310                 315                 320

Asn Asp Thr Gly Asn Tyr Phe Glu Gly Arg Pro Asn Gly Trp Glu Ser
        325                 330                 335

Met Glu Asp Ala Val Phe Val Val Ala Leu Leu Gln Ser Ala Gly Thr
    340                 345                 350

Val Gln Val Thr Ser Gly Pro Asn Thr Glu Thr Phe Asp Ala Pro Ala
355                 360                 365                 370

Gly Ala Ser Ala Phe Gln Val Pro Met Gly Phe Gly Pro Gln Ser Phe
                375                 380                 385

Ser Leu Ser Arg Asp Gly Glu Thr Val Leu Ser Gly Thr Ser Leu Lys
            390                 395                 400

Asp Ile Ile Asp Gly Cys Leu Cys Gly Ile Tyr Asn Phe Asn Ala Tyr
        405                 410                 415

Val Gly Ser Leu Pro Ala Thr Phe Ser Asp Pro Leu Glu Pro Pro Ser
    420                 425                 430

Leu Asn Ala Phe Ser Glu Gly Leu Lys Val Ser Thr Cys Ser Ala Thr
435                 440                 445                 450

Pro Ser Leu Gly Leu Thr Ser Thr Pro Pro Glu Thr Ile Pro Thr
                455                 460                 465

Gly Thr Ile Thr Pro Gly Ser Ala Ile Thr Gly Ala Ala Thr Thr Thr
        470                 475                 480

Ser Thr Ile Ser Thr Thr Ser Thr Ile Ser Thr Thr Ser Thr Phe Ile
        485                 490                 495

Ser Thr Thr Thr Thr Thr Thr Ser Ser Ala Ala Thr Ser Thr Thr Thr
    500                 505                 510

Gly Thr Cys Ile Ala Gly Thr Gly Pro Asp Asn Tyr Ser Gly Leu Cys
515                 520                 525                 530

Ser Phe Cys Cys Asn Tyr Gly Tyr Cys Pro Gly Ser Asp Gly Ser Ala
                535                 540                 545

Gly Pro Cys Thr Cys Thr Ala Tyr Gly Asp Pro Val Pro Thr Pro Pro
            550                 555                 560

Val Thr Gly Thr Val Gly Val Pro Leu Asp Gly Glu Gly Asp Ser Tyr
        565                 570                 575

Leu Gly Leu Cys Ser Phe Ala Cys Asn His Gly Tyr Cys Pro Ser Thr
```

| | | | | 580 | | | | | 585 | | | | | 590 | |
|---|---|---|---|---|---|---|---|---|---|---|---|---|---|---|---|

Ala Cys Gln Val Glu Ser
595             600

(2) INFORMATION FOR SEQ ID NO:4:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Ser Ser Ala Asp Arg Leu Val Phe Cys His Phe Met Ile Gly Ile Val
1               5                   10                  15

(2) INFORMATION FOR SEQ ID NO:5:

(i) SEQUENCE CHARACTERISTICS:
        (A) LENGTH: 635 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Met Leu Gly Val Phe Arg Arg Leu Arg Leu Gly Ala Leu Ala Ala Ala
1               5                   10                  15

Ala Leu Ser Ser Leu Gly Ser Ala Ala Pro Ala Asn Val Ala Ile Arg
                20                  25                  30

Ser Leu Glu Glu Arg Ala Ser Ala Asp Arg Leu Val Phe Cys His
                35                  40                  45

Phe Met Ile Gly Ile Val Gly Asp Arg Gly Ser Ser Ala Asp Tyr Asp
            50                  55                  60

Asp Asp Met Gln Arg Ala Lys Ala Ala Gly Ile Asp Ala Phe Ala Leu
65                  70                  75                  80

Asn Ile Gly Val Asp Gly Tyr Thr Asp Gln Gln Leu Gly Tyr Ala Tyr
                85                  90                  95

Asp Ser Ala Asp Arg Asn Gly Met Lys Val Phe Ile Ser Phe Asp Phe
                100                 105                 110

Asn Trp Trp Ser Pro Gly Asn Ala Val Gly Val Gly Gln Lys Ile Ala
            115                 120                 125

Gln Tyr Ala Asn Arg Pro Ala Gln Leu Tyr Val Asp Asn Arg Pro Phe
    130                 135                 140

Ala Ser Ser Phe Ala Gly Asp Gly Leu Asp Val Asn Ala Leu Arg Ser
145                 150                 155                 160

Ala Ala Gly Ser Asn Val Tyr Phe Val Pro Asn Phe His Pro Gly Gln
                165                 170                 175

Ser Ser Pro Ser Asn Ile Asp Gly Ala Leu Asn Trp Met Ala Trp Asp
                180                 185                 190

Asn Asp Gly Asn Asn Lys Ala Pro Lys Pro Gly Gln Thr Val Thr Val
                195                 200                 205

Ala Asp Gly Asp Asn Ala Tyr Lys Asn Trp Leu Gly Lys Pro Tyr
                210                 215                 220

Leu Ala Pro Val Ser Pro Trp Phe Phe Thr His Phe Gly Pro Glu Val
225                 230                 235                 240

Ser Tyr Ser Lys Asn Trp Val Phe Pro Gly Gly Pro Leu Ile Tyr Asn

-continued

```
                         245                            250                             255
        Arg  Trp  Gln  Gln  Val  Leu  Gln  Gln  Gly  Phe  Pro  Met  Val  Glu  Ile  Val
                       260                           265                           270

Thr  Trp  Asn  Asp  Tyr  Gly  Glu  Ser  His  Tyr  Val  Gly  Pro  Leu  Lys  Ser
                  275                           280                           285

Leu  His  Phe  Asp  Asp  Gly  Asn  Ser  Lys  Trp  Val  Asn  Asp  Met  Pro  His
                  290                           295                           300

Asp  Gly  Phe  Leu  Asp  Leu  Ser  Lys  Pro  Phe  Ile  Ala  Ala  Tyr  Lys  Asn
        305                           310                           315                 320

Arg  Asp  Thr  Asp  Ile  Ser  Lys  Tyr  Val  Gln  Asn  Glu  Gln  Leu  Val  Tyr
                                 325                           330                 335

Trp  Tyr  Arg  Arg  Asn  Leu  Lys  Ala  Leu  Asp  Cys  Asp  Ala  Thr  Asp  Thr
                            340                           345                      350

Thr  Ser  Asn  Arg  Pro  Ala  Asn  Asn  Gly  Ser  Gly  Asn  Tyr  Phe  Glu  Gly
                       355                           360                      365

Arg  Pro  Asp  Gly  Trp  Gln  Thr  Met  Asp  Asp  Ala  Val  Tyr  Val  Ala  Ala
                  370                           375                      380

Leu  Leu  Lys  Thr  Ala  Gly  Ser  Val  Thr  Ile  Thr  Ser  Gly  Gly  Thr  Thr
        385                           390                           395                 400

Gln  Thr  Phe  Gln  Ala  Asn  Ala  Gly  Ala  Asn  Leu  Phe  Gln  Ile  Pro  Ala
                                 405                           410                 415

Ser  Ile  Gly  Gln  Gln  Lys  Phe  Ala  Leu  Thr  Arg  Asn  Gly  Gln  Thr  Ile
                            420                           425                      430

Phe  Ser  Gly  Thr  Ser  Leu  Met  Asp  Ile  Thr  Asn  Val  Cys  Ser  Cys  Gly
                       435                           440                      445

Ile  Tyr  Asn  Phe  Asn  Pro  Tyr  Val  Gly  Thr  Ile  Pro  Ala  Gly  Phe  Asp
                  450                           455                      460

Asp  Pro  Leu  Gln  Ala  Asp  Gly  Leu  Phe  Ser  Leu  Thr  Ile  Gly  Leu  His
        465                           470                           475                 480

Val  Thr  Thr  Cys  Gln  Ala  Lys  Pro  Ser  Leu  Gly  Thr  Asn  Pro  Pro  Val
                                 485                           490                 495

Thr  Ser  Gly  Pro  Val  Ser  Ser  Leu  Pro  Ala  Ser  Ser  Thr  Thr  Arg  Ala
                            500                           505                      510

Ser  Ser  Pro  Pro  Pro  Val  Ser  Thr  Arg  Val  Ser  Ser  Pro  Pro  Val
                       515                           520                      525

Ser  Ser  Pro  Pro  Val  Ser  Arg  Thr  Ser  Ser  Pro  Pro  Pro  Pro  Ala
                  530                           535                      540

Ser  Ser  Thr  Pro  Pro  Ser  Gly  Gln  Val  Cys  Val  Ala  Gly  Thr  Val  Ala
        545                           550                           555                 560

Asp  Gly  Glu  Ser  Gly  Asn  Tyr  Ile  Gly  Leu  Cys  Gln  Phe  Ser  Cys  Asn
                                 565                           570                 575

Tyr  Gly  Tyr  Cys  Pro  Pro  Gly  Pro  Cys  Lys  Cys  Thr  Ala  Phe  Gly  Ala
                            580                           585                      590

Pro  Ile  Ser  Pro  Pro  Ala  Ser  Asn  Gly  Arg  Asn  Gly  Cys  Pro  Leu  Pro
                       595                           600                      605

Gly  Glu  Gly  Asp  Gly  Tyr  Leu  Gly  Leu  Cys  Ser  Phe  Ser  Cys  Asn  His
                  610                           615                      620

Asn  Tyr  Cys  Pro  Pro  Thr  Ala  Cys  Gln  Tyr  Cys
        625                           630                      635
```

( 2 ) INFORMATION FOR SEQ ID NO:6:

( i ) SEQUENCE CHARACTERISTICS:
        ( A ) LENGTH: 32 base pairs
        ( B ) TYPE: nucleic acid

```
            ( C ) STRANDEDNESS: single
            ( D ) TOPOLOGY: linear ( i i ) MOLECULE TYPE: cDNA ( x i ) SEQUENCE DESCRIPTION: SEQ ID NO:6:

CCCATTTAAA  TATGAAAGTC  TCCAGTGCCT  TC                                          3 2

( 2 ) INFORMATION FOR SEQ ID NO:7:

( i ) SEQUENCE CHARACTERISTICS:
            ( A ) LENGTH: 32 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:7:

CCCTTAATTA  ATTAGCTCTC  TACTTGACAA  GC                                          3 2
```